(12) United States Patent
Ma et al.

(10) Patent No.: US 11,241,677 B2
(45) Date of Patent: Feb. 8, 2022

(54) POLYOXOMETALATES COMPRISING NOBLE METALS AND POST-TRANSITION METALS AND METAL CLUSTERS THEREOF

(71) Applicant: ExxonMobil Chemical Patents Inc., Baytown, TX (US)

(72) Inventors: Tian Ma, Bremen (DE); Ulrich Kortz, Bremen (DE); Peng Yang, Thuwal (SA); Zhengguo Lin, Beijing (CN); Wassim W. Ayass, Berlin (DE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 140 days.

(21) Appl. No.: 16/490,270

(22) PCT Filed: Jan. 25, 2018

(86) PCT No.: PCT/EP2018/051870
§ 371 (c)(1),
(2) Date: Aug. 30, 2019

(87) PCT Pub. No.: WO2018/162144
PCT Pub. Date: Sep. 13, 2018

(65) Prior Publication Data
US 2020/0070131 A1 Mar. 5, 2020

(30) Foreign Application Priority Data
Mar. 8, 2017 (EP) .................... 17159815

(51) Int. Cl.
*C01G 55/00* (2006.01)
*B01J 27/185* (2006.01)
(Continued)

(52) U.S. Cl.
CPC ....... *B01J 27/1856* (2013.01); *B01J 37/0215* (2013.01); *B01J 37/16* (2013.01);
(Continued)

(58) Field of Classification Search
CPC ...... B01J 37/0215; B01J 37/348; B01J 37/16; B01J 37/34; B01J 37/02; B01J 27/1856;
(Continued)

(56) References Cited

U.S. PATENT DOCUMENTS 4,864,041 A 9/1989 Hill
2005/0112055 A1 5/2005 Shannon et al.
(Continued)

FOREIGN PATENT DOCUMENTS

WO 2007/139616 A 12/2007
WO 2007/142727 A 12/2007
(Continued)

OTHER PUBLICATIONS

Barsukova-Stuckart et al., "3d Metal Ions in Highly Unusual Eight-Coordination: The Phosphate-Capped Dodecapalladate(II) Nanocube", Chem Eur. J., 2012, vol. 18, pp. 6167-6171.
(Continued)

*Primary Examiner* — Smita S Patel

(57) ABSTRACT

The invention relates to polyoxometalates represented by the formula $(A_n)^{m+}[M'M_{12}X_8O_yR_zH_q]^{m-}$ or solvates thereof, corresponding supported polyoxometalates, and processes for their preparation, as well as corresponding metal clusters, optionally in the form of a dispersion in a liquid carrier medium or immobilized on a solid support, and processes for their preparation, as well as their use in reductive conversion of organic substrate.

7 Claims, 5 Drawing Sheets

Figure 1:
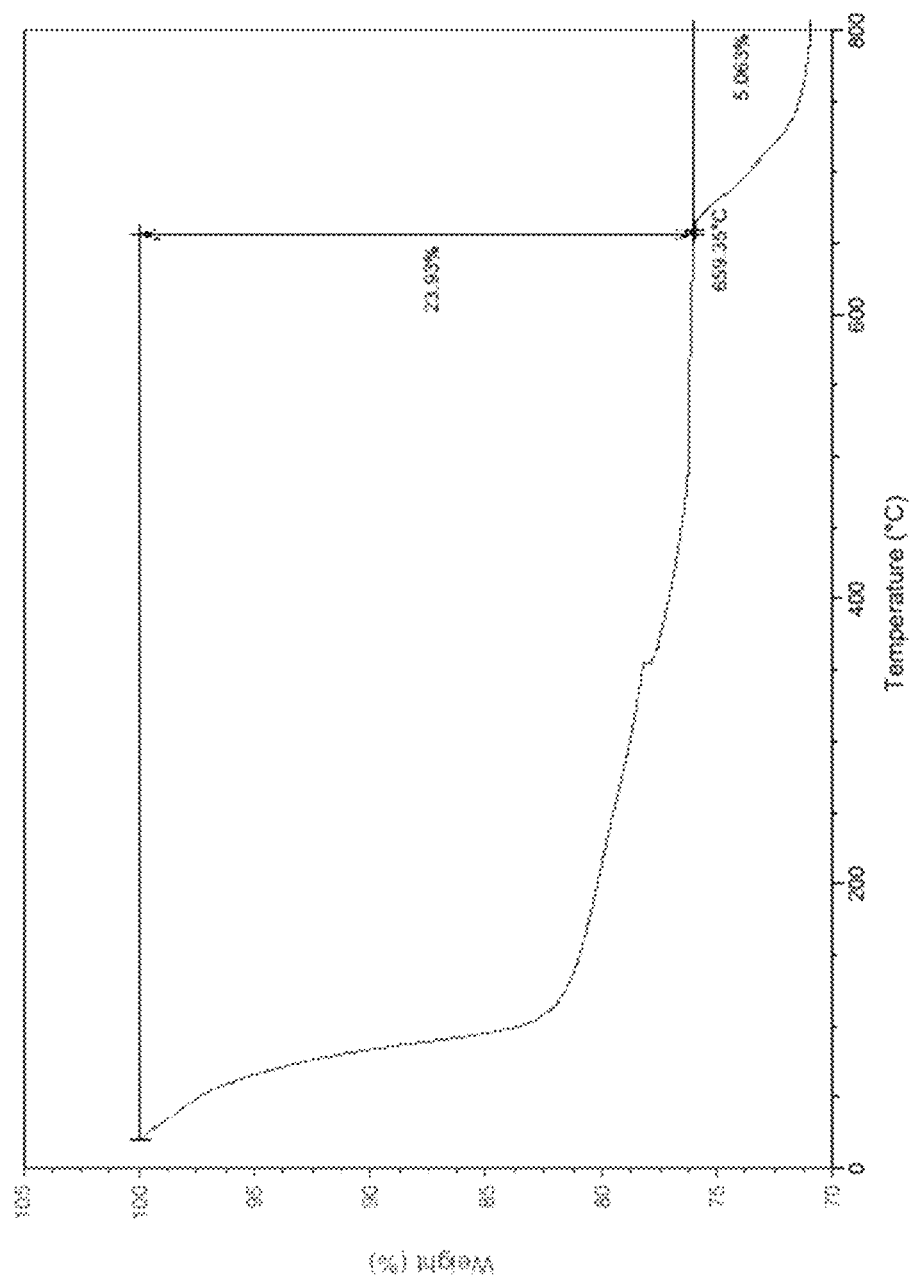

(51) Int. Cl.
*B01J 37/02* (2006.01)
*B01J 37/16* (2006.01)
*B01J 37/34* (2006.01)
*C07C 5/10* (2006.01)

(52) U.S. Cl.
CPC .......... *B01J 37/348* (2013.01); *C01G 55/002* (2013.01); *C07C 5/10* (2013.01); *C01P 2002/72* (2013.01); *C01P 2002/76* (2013.01); *C01P 2002/82* (2013.01); *C01P 2002/86* (2013.01); *C01P 2002/88* (2013.01); *C07C 2523/04* (2013.01); *C07C 2523/14* (2013.01); *C07C 2523/44* (2013.01); *C07C 2527/185* (2013.01); *C07C 2601/14* (2017.05)

(58) Field of Classification Search
CPC . B01J 27/138; B01J 27/13; B01J 27/14; B01J 27/1813; B01J 27/1806; B01J 2523/824; B01J 2523/828; B01J 2523/82; B01J 2523/51; B01J 2523/43; B01J 2523/44; B01J 2523/42; B01J 2523/11; B01J 2523/12; B01J 2523/13; C07C 2527/14; C07C 2527/167; C07C 2527/16; C07C 2527/185; C07C 2601/14; C07C 5/10; C01P 2002/88; C01P 2002/82; C01P 2002/86; C01P 2002/72; C01P 2002/76; C01G 17/00; C01G 55/00; C01G 55/002; C01G 21/00; C01G 21/16
USPC .................................................. 502/306, 326
See application file for complete search history.

(56) References Cited

U.S. PATENT DOCUMENTS

2009/0216052 A1    8/2009  Chubarova et al.
2019/0091663 A1*   3/2019  Kortz ....................... B01J 21/08

FOREIGN PATENT DOCUMENTS

| WO | 2007/142729 A | 12/2007 |
| WO | 2008/089065 A | 7/2008 |
| WO | 2008/118619 A | 10/2008 |
| WO | 2009/155185 A | 12/2009 |
| WO | 2010/021600 A | 2/2010 |

OTHER PUBLICATIONS

Barsukova-Stuckart et al., "Polyoxopalladates Encapsulating 8-Coordinated Metal Ions, $[MO_8Pd^{II}_{12}L_8]^{n-}$ (M=$Sc^{3-}$, $Mn^{2+}$, $Fe^{3+}$, $Co^{2+}$, $Ni^{2+}$, $Cu^{2+}$, $Zn^{2+}$, $Lu^{3+}$; L=$PhAsO_3^{2-}$, $PhPO_3^{2-}$, $SeO_3^{2-}$)", Inorg. Chem., 2012, vol. 51, pp. 13214-13228.

Cameron et al., "Self-assembly and structural transformations of high-nuclearity palladium-rich polyoxometalates", Inorg. Chem. Front., 2014, vol. 1, pp. 178-185.

Chubarova et al., "Self-Assembly of a Heteropolyoxopalladate Nanocube: $[Pd^{II}_{13}As^{V}_{8}O_{34}(OH)_6]^{8-}$", Angew. Chem. Int. Ed., 2008, vol. 47, pp. 9542-9546.

Izarova et al., "Noble Metals in Polyoxometalates", Angew. Chem. Int. Ed., 2012, vol. 51, pp. 9492-9510.

Izarova et al., "The Mixed Gold-Palladium Polyoxo-Noble-Metalate $[NaAu^{III}_4Pd^{II}_8O_8(AsO_4)_8]^{11-}$", Chem. Eur. J., 2014, vol. 20, pp. 8556-8560.

Lin et al., "Controlled Synthesis of Polyoxopalladates, and Their Gas-Phase Fragmentation Study by Electrospray Ionization Tandem Mass Spectrometry", Eur. J. Inorg. Chem., 2013, vol. 2013, No. 20, pp. 3458-3463.

Putaj et al., "Polyoxometales containing late transition and noble metal atoms", Coord. Chem. Rev., 2011, vol. 255, pp. 1642-1685.

Kortz, "Germany: Polyoxopalladate Pioneer of Materials Research", Process Worldwide, 2017, Jacobs University Bremen GmbH.

* cited by examiner

POLYOXOMETALATES COMPRISING NOBLE METALS AND POST-TRANSITION METALS AND METAL CLUSTERS THEREOF

CROSS REFERENCE TO RELATED APPLICATIONS

This application is a National Stage Application of International Application No. PCT/EP2018/051870, filed Jan. 25, 2018, which claims priority to and the benefit of European Patent Application Serial No. 17159815.4, filed Mar. 8, 2017, which are incorporated herein by reference in their entireties.

FIELD OF THE INVENTION

This invention relates to new polyoxometalates (POMs) and metal clusters. Furthermore, this invention relates to processes for the preparation of said new POMs and metal clusters and to their use in catalytic reduction reactions with organic molecules.

BACKGROUND OF THE INVENTION

POMs (also known as polyanions) are a unique class of inorganic metal-oxygen clusters. They consist of a polyhedral cage structure or framework bearing a negative charge which is balanced by cations that are usually external to the cage, and may also contain internally or externally located heteroatom(s) or guest atom(s). The framework of POMs comprises a plurality of metal atoms, which can be the same or different, bonded to oxygen atoms. In the plurality of known POMs the framework metals are dominated by a few elements including transition metals from Group 5 and Group 6 in their high oxidation states, e.g. tungsten (VI), molybdenum (VI), vanadium (V), niobium (V) and tantalum (V).

The first example in the POM family is the so-called Keggin anion $[XC_{12}O_{40}]^{n-}$ with X being a heteroatom selected from a variety of elements, e.g. P, and M being a Group 5 or Group 6 metal such as Mo or W. These anions consist of an assembly of corner- and edge-shared $MO_6$ octahedra of the metals of Groups 5 or 6 around a central $XO_4$ tetrahedron.

There have been increasing efforts towards the modification of POMs with various organic and/or transition metal complex moieties with the aim of generating new catalyst systems as well as functional materials with interesting optical, electronic, magnetic and medicinal properties. In particular, transition metal-substituted POMs (TMSPs) have attracted continuously growing attention as they can be rationally modified on the molecular level including size, shape, charge density, acidity, redox states, stability, solubility etc. To date many 3 d transition metal-containing POMs are known, but still only a minority of POMs contains 4 d and 5 d metals. However, the introduction of 4 d and 5 d metals, especially of late 4 d and 5 d metals, in a POM would be of fundamental interest en route to new, more efficient and more selective catalysts. Especially Rh, Ir, Pd, Pt, Ag and/or Au-containing POMs would be of high interest, because they are thermally and oxidatively stable and possess highly attractive catalytic properties.

For example, Kortz and coworkers reported the first molecular palladium-oxo polyanion $[Pd_{13}As_8O_{34}(OH)_6]^{8-}$ in 2008 (Angew. Chem. Int. Ed. 2008, 47, 9542-9546). Twelve palladium atoms surround the thirteenth, the central palladium atom, resulting in a distorted icosahedral arrangement. In US 2009/0216052 A1 closely related POMs are disclosed based on this common structural motif comprising $[M_{13}X_8R_qO_y]^{m-}$ with M being selected from Pd, Pt, Au, Rh, Ir, and mixtures thereof, while X is a heteroatom such as As, Sb, Bi, P, Si, Ge, B, Al, Ga, S, Se, Te, and mixtures thereof. These POMs were demonstrated to be useful as catalysts and precursors for mixed metal-oxide catalysts and metal clusters (also referred to as metal-clusters).

Kortz and coworkers also developed a related class of POMs displaying a similar structural arrangement but a different elemental composition. In the $[MPd_{12}P_8O_{40}H_z]^{m-}$ polyanions the 'inner' '$MO_8$' motif is surrounded by twelve square-planar '$PdO_4$' units and M is represented by $Mn^{II}$, $Fe^{III}$, $Co^{II}$, $Cu^{II}$ and $Zn^{III}$ (Chem. Eur. J. 2012, 18, 6167-6171).

In this context, Kortz and coworkers found that in the $[MO_8Pd_{12}L_8]^{n-}$ polyanions the cuboidal $\{Pd_{12}O_8L_8\}$ shell incorporates 8-fold coordinated guest metal ions M being selected from $Sc^{III}$, $Mn^{II}$, $Fe^{III}$, $Co^{II}$, $Ni^{II}$, $Cu^{II}$, $Zn^{II}$ and $Lu^{III}$, while L is represented by $PhAsO_3^{2-}$, $PhPO_3^{2-}$ or $SeO_3^{2-}$ (Inorg. Chem. 2012, 51, 13214-13228).

In 2014 Kortz and coworkers published the first fully inorganic discrete gold-palladium-oxo polyanion $[NaAu_4Pd_8O_8(AsO_4)_8]^{11-}$ without the stabilization of any organic ligands and with both Au and Pd occupying the atom positions of the metal framework. With regard to the structure, the cubic '$NaO_8$' moiety is surrounded by 12 noble metal centers forming a cuboctahedron, which is capped by eight tetrahedral arsenate groups (Chem. Eur. J. 2014, 20, 8556-8560).

Cronin and coworkers found three new Pd-containing POMs $K_{28}[H_{12}Pd_{10}Se_{10}W_{52}O_{206}]$, $K_{26}[H_{12}Pd_{10}Se_{10}W_{52}O_{206}]$ and $Na_{40}[Pd_6Te_{19}W_{42}O_{190}]$ demonstrating the structural complexity of some of the late transition metal-containing POMs (Inorg. Chem. Front. 2014, 1, 178-185).

WO 2007/142729 A1 discloses a class of Pd and W as well as Pt and W-based POMs and mixtures thereof with the general formula $[M_y(H_2O)_{(p\bullet y)}X_2W_{22}O_{74}(OH)_2]^{m-}$ with M being Pd, Pt, and mixtures thereof, y being 1 to 4, p being the number of water molecules bound to one M and being 3 to 5 and X being Sb, Bi, As, Se and Te. Protocols for the preparation of these POMs were provided. Furthermore, the POMs were found to be useful as catalysts.

WO 2008/089065 A1 discloses a class of W-based POMs including late transition metals with the formula $[M_y(H_2O)_p X_zZ_2W_{18}O_{66}]^{m-}$ with M being Cu, Zn, Pd and Pt, X being selected from the group of halides and Z being Sb, Bi, As, Se and Te. The POMs prepared are useful as catalysts.

WO 2007/142727 A1 discloses a class of transition metal-based POMs including W having the formula $[M_4(H_2O)_{10}(XW_9O_{33})_2]^{m-}$ with M being a transition metal and X being selected from As, Sb, Bi, Se and Te. These POMs are particularly useful as catalysts featuring high levels of conversion in selective alkane oxidation.

WO 2008/1118619 A1 discloses another class of transition metal-based POMs including W which is illustrated by the general formula $[H_qM_{16}X_8W_{48}O_{184}(HO)_{32}]^{m-}$ with M being selected from the group of transition metals and X being selected from As and/or P. Protocols for the preparation of these POMs were developed. Furthermore, the POMs were found to be useful as catalysts.

US 2005/0112055 A1 discloses a POM including three different transition metals Ru, Zn and W with the formula $Na_{14}[Ru_2Zn_2(H_2O)_2(ZnW_9O_{34})_2]$. This particular POM was found to be highly efficient as an electrocatalyst in the generation of oxygen.

WO 2007/139616 A1 discloses a class of W-based POMs including Ru with the formula $[Ru_2(H_2O)_6X_2W_{20}O_{70}]^{m-}$ with X being selected from Sb, Bi, As, Se, and Te. Protocols for the preparation of these POMs are described. Furthermore, the POMs were found to be useful as catalysts.

WO 2009/155185 A1 discloses a class of Ru and W-based POMs provided by the general formula $[Ru_2L_2(XW_{11}O_{39})_2WO_2]^{m-}$ with L being a ligand and X being Si, Ge, B and mixtures thereof. The POMs are useful as catalysts and precursors for the preparation of mixed metal-oxide catalysts.

U.S. Pat. No. 4,864,041 in general demonstrates the potential of POMs as catalysts for the oxidation of organic compounds. A variety of different POMs with different metal species was investigated, including those with W, Mo, V, Cu, Mn, Fe, and Co.

WO 2010/021600 A1 discloses a method for preparing POMs and reducing them. Thus, for example metallic nanoparticles can be derived. Specifically W-based POMs are discussed.

Two reviews on POM containing late transition metals and noble metals (Coord. Chem. Rev. 2011, 255, 1642-1685 and Angew. Chem. Int. Ed. 2012, 51, 9492-9510) reveal that, although there is a noticeable development in this area in recent years and decades, the POMs containing noble metals are almost exclusively still based on early transition metals, including Group 5 and 6 metals. Very few of these POMs are solely based on noble metals. In many cases the noble metals are incorporated in structural frameworks primarily composed of early transition metals, including Group 5 and 6 metals.

Thus, there is a need for new POMs containing a major proportion of metals other than early transition metals, based on the overall metal content of said POMs, and possessing useful properties in homogeneous or heterogeneous catalytic applications. In this regard, particularly those POMs which contain mixed metals and in particular a major proportion of noble metals, i.e., which contain a major proportion of noble metal atoms doped with a minor proportion of other metal atoms than noble metal atoms, and those which contain more than one different type of noble metal atom species doped with other metals are highly promising candidates en route to new, more efficient and more selective catalysts due to the well-established unique catalytic properties of noble metals.

Therefore, it is an object of the present invention to provide POMs containing inter alia a major proportion of noble metal atoms doped with other metals, based on the overall metal content of said POMs. Furthermore, it is an object of the present invention to provide one or multiple processes for the preparation of said POMs. In addition, it is an object of the present invention to provide supported POMs containing a major proportion of noble metal atoms, based on the overall metal content of said POMs as well as one or multiple processes for the preparation of said supported POMs. Another object of the present invention is the provision of metal clusters, in particular the provision of highly dispersed metal cluster particles, and processes for the preparation of said metal clusters either in the form of a dispersion in a liquid carrier medium or in supported form, immobilized on a solid support. Finally, it is an object of the present invention to provide one or multiple processes for the homogeneous or heterogeneous reductive conversion of organic substrates using said optionally supported POM(s) and/or said optionally supported or dispersed metal cluster(s).

SUMMARY OF THE INVENTION

An objective of the present invention among others is achieved by the provision of POMs represented by the formula

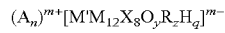

or solvates thereof, wherein
each A independently represents a cation,
n is the number of cations,
each M is independently selected from the group consisting of Pd, Pt, Rh, Ir, Ag and Au, and each M has $d^8$ valence electron configuration,
M' is selected from the group consisting of Ga, In, Tl, Ge, Sn, Pb, Sb, and Bi,
each X is independently selected from the group consisting of Al, Si, P, As, S, Se, Te and mixtures thereof,
each R is a substituent group which is covalently bonded to X, and each R is independently selected from the group consisting of a hydrogen atom, a substituent group bonded to X via a carbon atom of said substituent group, a substituent group bonded to X via an oxygen atom of said substituent group, a substituent group bonded to X via a sulphur atom of said substituent group, and a substituent group bonded to X via a nitrogen atom of said substituent group,
y is a number from 32 to 40,
z is a number from 0 to 8,
q is a number from 0 to 16, and
m is a number representing the total positive charge m+ of n cations A and the corresponding negative charge m− of the polyanion $[M'M_{12}X_8O_yR_zH_q]$.

These noble metal- and post-transition metal-containing POMs are based on square planar $MO_4$ building blocks wherein each M has a $d^8$ valence electron configuration. Based on the $d^8$ valence electron configuration, the oxidation state of the respective M can be identified, so that M is $Pd^{II}$, $Pt^{II}$, $Rh^{I}$, $Ir^{I}$, $Ag^{III}$ or $Au^{III}$. Hence the requirement for M having a $d^8$ valence electron configuration is synonymous to M being selected from the group consisting of $Pd^{II}$, $Pt^{II}$, $Rh^{I}$, $Ir^{I}$, $Ag^{III}$, and $Au^{III}$.

An objective of the present invention among others is achieved by the provision of a process for the preparation of any one of the POMs provided by the present invention, said process comprising:
(a) reacting at least one source of M, and at least one source of M' with at least one X-containing and optionally R-containing starting material to form a salt of the polyanion $[M'M_{12}X_8O_yR_zH_q]$ or a solvate thereof,
(b) optionally adding at least one salt of A to the reaction mixture of step (a) to form a polyoxometalate $(A_n)^{m+}[M'M_{12}X_8O_yR_zH_q]^{m-}$ or a solvate thereof, and
(c) recovering the polyoxometalate or solvate thereof.

An objective of the present invention among others is achieved by the provision of supported POMs comprising any one of the POMs provided by the present invention or prepared according to the present invention, on a solid support.

An objective of the present invention among others is achieved by the provision of a process for the preparation of the supported POMs provided by the present invention, said process comprising the step of contacting any one of the POMs provided by the present invention or prepared according to the present invention, with a solid support.

An objective of the present invention among others is achieved by the provision of metal clusters of the formula

wherein
- each $M^o$ is independently selected from the group consisting of $Pd^o$, $Pt^o$, $Rh^o$, $Ir^o$, $Ag^o$, and $Au^o$, preferably $Pd^o$ and $Pt^o$, most preferably $Pd^o$; in particular wherein all $M^o$ are the same, preferably wherein all $M^o$ are $Pd^o$, and
- M' is selected from the group consisting of Ga, In, Tl, Ge, Sn, Pb, Sb, and Bi, and the oxidation state of M' is 0 or greater than 0, preferably M' is Sn, most preferably $Sn^o$.

An objective of the present invention among others is achieved by the provision of the metal clusters provided by the present invention in the form of a dispersion in a liquid carrier medium.

An objective of the present invention among others is achieved by the provision of supported metal clusters comprising any one of the metal clusters provided by the present invention immobilized on a solid support.

An objective of the present invention among others is achieved by the provision of a process for the preparation of any one of the metal clusters provided by the present invention, in the form of a dispersion of said metal clusters dispersed in a liquid carrier medium, said process comprising the steps of
- (a) dissolving any one of the POMs provided by the present invention or prepared according to the present invention in a liquid carrier medium,
- (b) optionally providing additive means to prevent agglomeration of the metal cluster to be prepared, and
- (c) subjecting the dissolved POM to chemical or electrochemical reducing conditions sufficient to at least partially reduce said POM into corresponding metal clusters.

An objective of the present invention among others is achieved by the provision of a process for the preparation of supported metal clusters, i.e. any one of the metal clusters provided by the present invention, in the form of metal clusters immobilized on a solid support, said process comprising the steps of
- (a) contacting the dispersion of metal clusters provided by the present invention or prepared according to the present invention, with a solid support, thereby immobilizing at least part of the dispersed metal clusters onto the support and obtaining supported metal clusters; and
- (b) optionally isolating the supported metal clusters.

An objective of the present invention among others is achieved by the provision of a process for the preparation of supported metal clusters, i.e. any one of the metal clusters provided by the present invention, in the form of metal clusters immobilized on a solid support, said process comprising the steps of
- (a) subjecting any one of the supported POM provided by the present invention or prepared according to the present invention to chemical or electrochemical reducing conditions sufficient to at least partially reduce said POM into corresponding metal clusters provided by the present invention; and
- (b) optionally isolating the supported metal clusters.

An objective of the present invention among others is achieved by the provision of a process for the homogeneous or heterogeneous reductive conversion of organic substrate comprising contacting said organic substrate under addition of hydrogen with any one of the optionally supported POMs provided by the present invention or prepared according to the present invention, and/or with any one of the optionally dispersed or supported metal clusters provided by the present invention or prepared according to the present invention.

In the context of the present invention the term noble metal comprises the following elements: Rh, Ir, Pd, Pt, Ag, and Au.

In the context of the present invention the term post-transition metal comprises the following elements: Ga, In, Tl, Ge, Sn, Pb, Sb, and Bi.

With regard to the present invention the expressions Group 1, Group 2, Group 3 etc. refer to the Periodic Table of the Elements and the expressions 3 d, 4 d and 5 d metals refer to transition metals of respective Periods 4, 5 and 6 of the Periodic Table of the Elements, i.e., the 4 d metal in Group 10 is Pd.

With regard to the present invention the term cuboctahedron describes the structural arrangement of the 12 M atoms in $(A_n)^{m+}[M'M_{12}X_8O_yR_zH_q]^{m-}$.

With regard to the present invention the term guest atom describes the centrally located M' atom within the cuboctahedron in $(A_n)^{m+}[M'M_{12}X_8O_yR_zH_q]^{m-}$.

With regard to the present invention the term polyanion describes the negatively charged structural arrangement $[M'M_{12}X_8O_yR_zH_q]$.

With regard to the present invention the term metal cluster describes the structural arrangement $[M'M^o{}_{12}]$.

With regard to the present invention the term nanocube describes the structural arrangement formed by the M, M' and X atoms $M'M_{12}X_8$.

With regard to the present invention the term immobilizing means to render immobile or to fix the position. In the context of a solid support the term immobilizing describes the adhesion to a surface by means of adsorption, including physisorption and chemisorption. Adsorption is based on interactions between the material to be adsorbed and the surface of the solid support such as van-der-Waals interactions, hydrogen-bonding interactions, ionic interactions, etc.

With regard to the present invention the expression primary particles of POM or POMs primary particles describes isolated particles that contain exactly one negatively charged polyanion $[M'M_{12}X_8O_yR_zH_q]$. The POMs primary particles of the present invention are substantially mono-dispersed particles, i.e. the POMs primary particles have a uniform size, corresponding to the size of one polyanion. The expression POMs secondary particles describes agglomerates of POMs primary particles.

With regard to the present invention the term supported POMs describes POMs immobilized on a solid support.

With regard to the present invention the expression primary particles of metal cluster or metal cluster primary particles describes isolated particles that contain exactly one metal cluster $[M'M^o{}_{12}]$. The metal cluster primary particles of the present invention are substantially mono-dispersed particles, i.e. the metal cluster primary particles have a substantially uniform size, corresponding to the size of one metal cluster. The expression metal cluster secondary particles describes agglomerates of metal cluster primary particles.

The particle size of the non-aggregated and aggregated POMs, and of the non-aggregated and aggregated metal clusters, respectively, can be determined by various physical methods known in the art. If the particles are dispersed in a liquid medium, the particle size can be determined by light scattering. If the particles are supported on a solid support, solid state techniques are required for determining the particle size of the supported particles, and to distinguish between primary particles (non-aggregated) and secondary particles (aggregated). Suitable solid state techniques include scanning electron microscopy (SEM), transmission electron microscopy (TEM), powder X-ray diffraction or crystallography (powder XRD), etc.

Another suitable technique for determining the particle size is pulsed chemi-/physisorption.

With regard to the present invention the term supported metal cluster describes metal clusters immobilized on a solid support.

BRIEF DESCRIPTION OF THE FIGS. 1-4

FIG. 1: Thermogravimetric analysis (TGA) curve of $Na_{12}[SnPd_{12}P_8O_{40}]\cdot43H_2O$ ("Na—$SnPd_{12}$") from 20° C. to 800° C.

Figure 2:
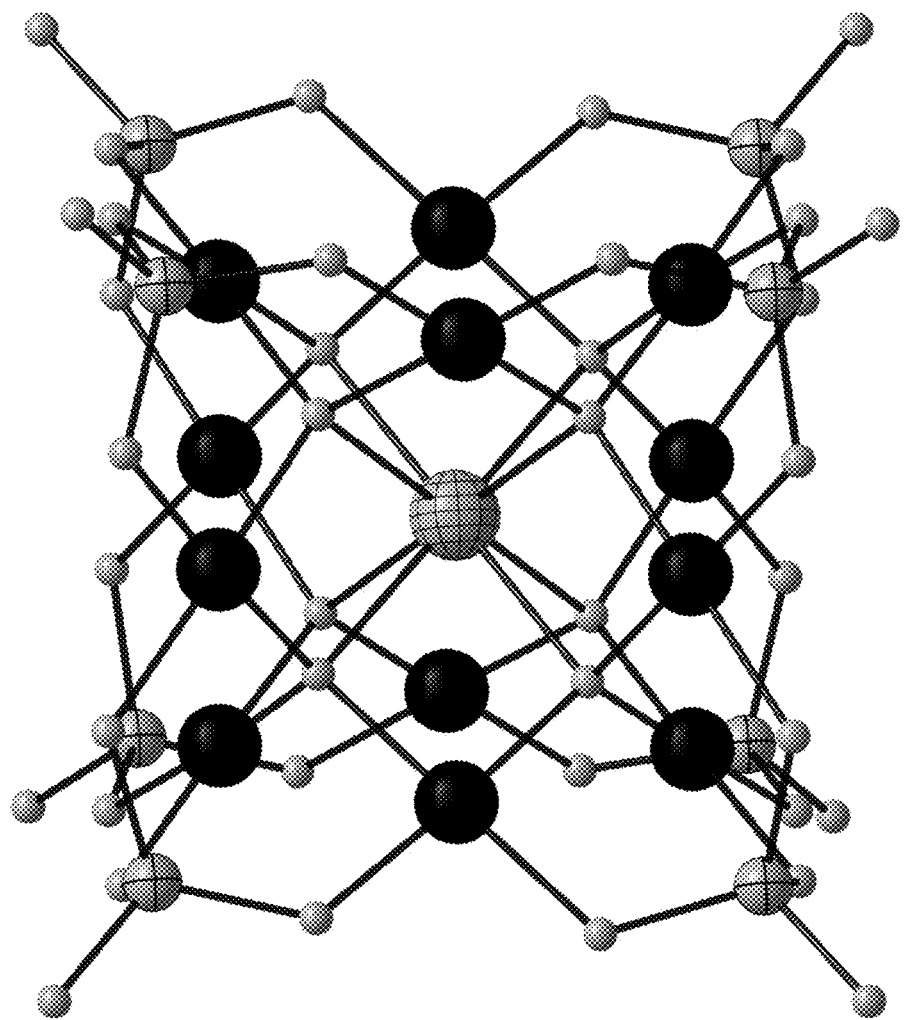

FIG. 2: Ball-and-stick representation of the $[SnPd_{12}P_8O_{40}]^{12-}$ polyanion ("$SnPd_{12}$"). Legend: Pd, black spheres; Sn, grey spheres with gridding; P, grey spheres with cross-line; O, grey spheres.

Figure 3:
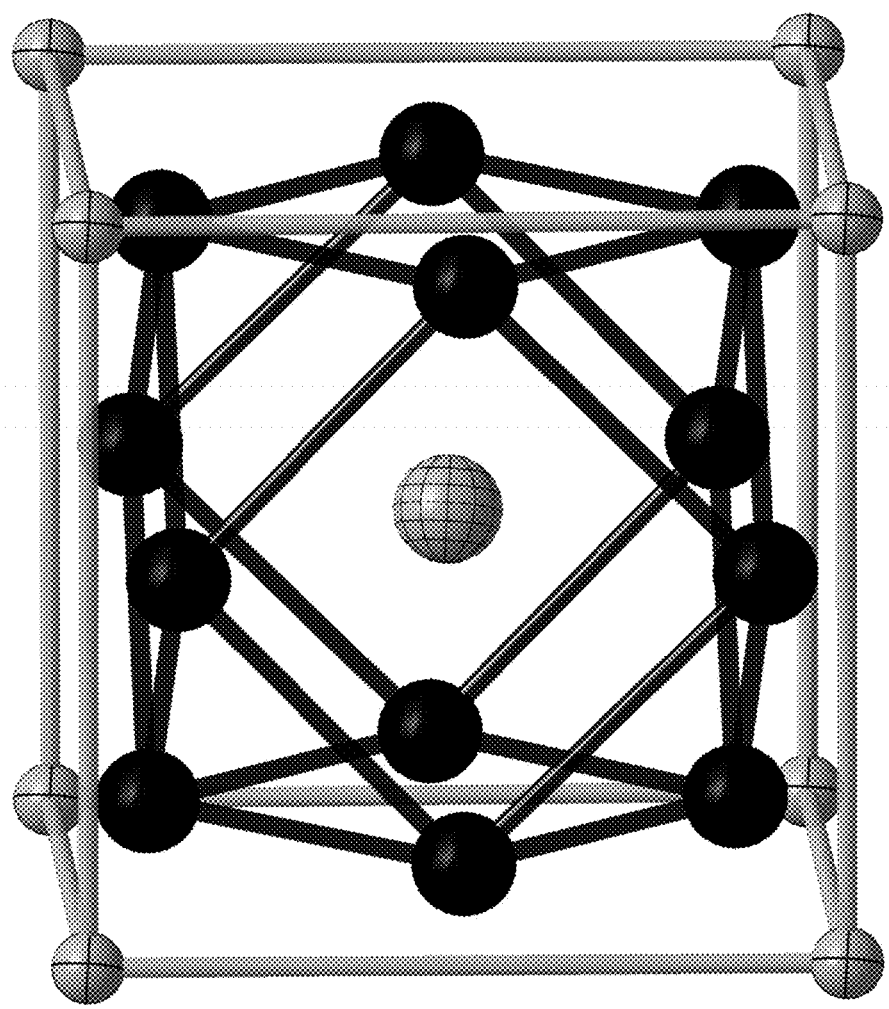

FIG. 3: P/Pd/Sn skeleton of the $[SnPd_{12}P_8O_{40}]^{12-}$ polyanion ("$SnPd_{12}$"). Legend: Pd, black spheres; Sn, grey spheres with gridding; P, grey spheres with cross-line.

Figure 4:
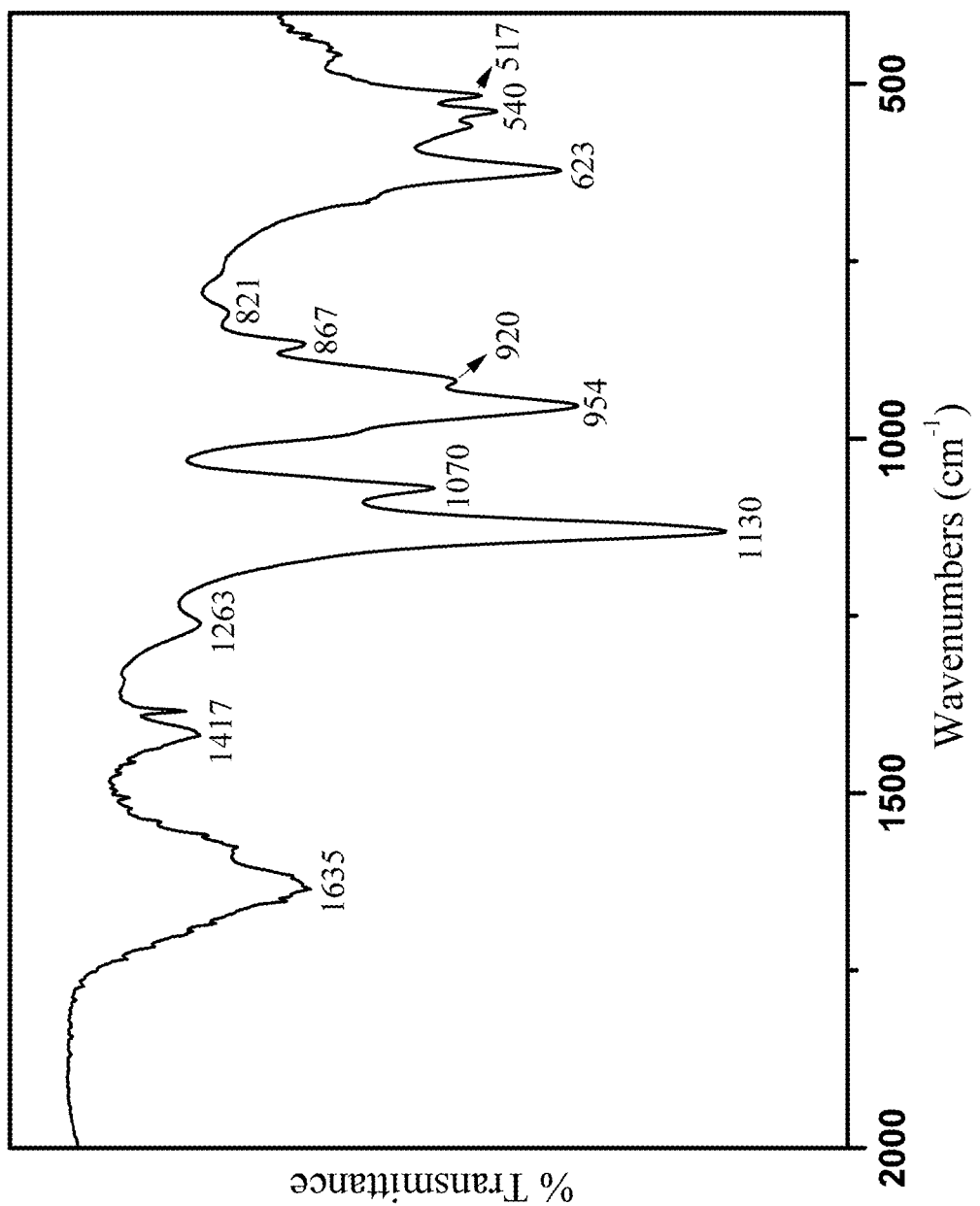

FIG. 4: Fourier Transform Infrared (FT-IR) spectrum of $Na_{12}[SnPd_{12}P_8O_{40}]\cdot43H_2O$ ("Na—$SnPd_{12}$")

Figure 5:
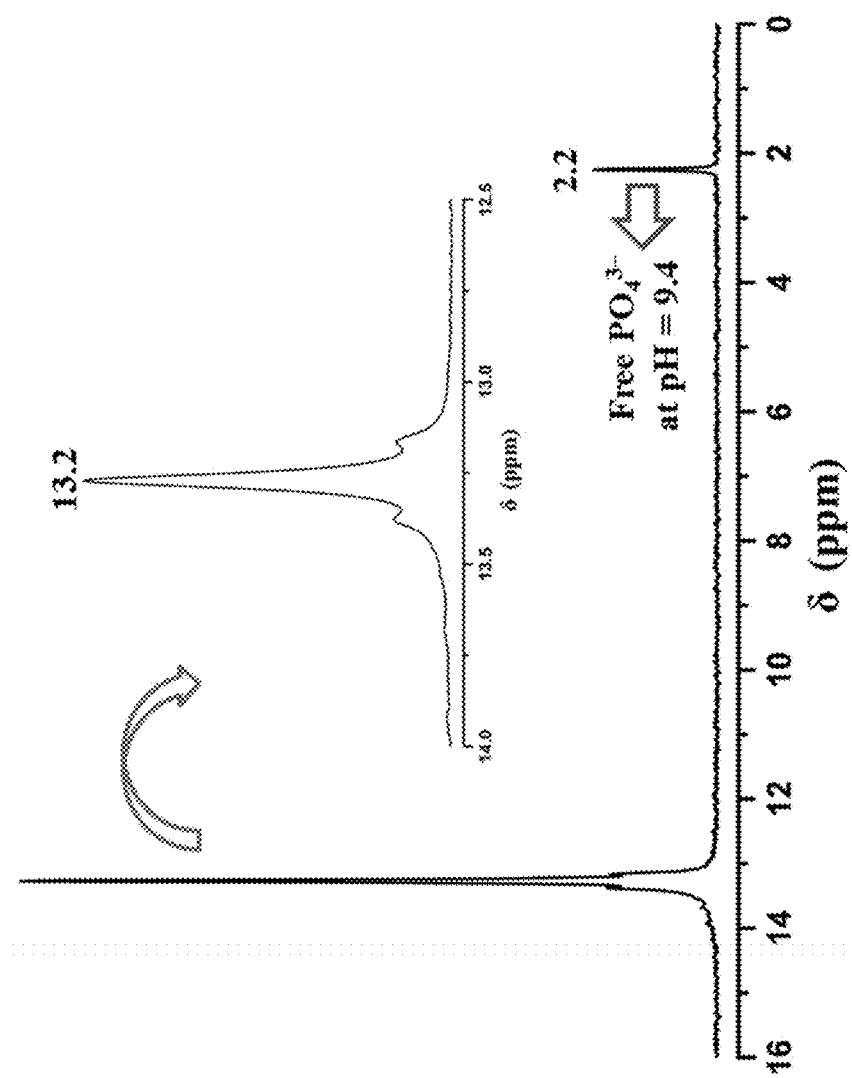

FIG. 5: $^{31}$P NMR spectrum of $Na_{12}[SnPd_{12}P_8O_{40}]\cdot43H_2O$ ("Na—$SnPd_{12}$")

DETAILED DESCRIPTION

According to one embodiment, the POMs of the present invention are represented by the formula

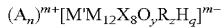

or solvates thereof, wherein
each A independently represents a cation, preferably each A is independently selected from the group consisting of cations of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Sn, Sb, Te; or phosphonium, ammonium, guanidinium, tetraalkylammonium, protonated aliphatic amines, protonated aromatic amines, or combinations thereof; more preferably, A is selected from lithium, potassium, sodium cations and combinations thereof,
n is the number of cations,
each M is independently selected from the group consisting of Pd, Pt, Rh, Ir, Ag, and Au, preferably Pd, Pt, Rh, Ir, and Au, more preferably Pd, Pt and Rh, most preferably Pd and Pt, in particular Pd, and each M has $d^8$ valence electron configuration,
M' is selected from the group consisting of Ga, In, Tl, Ge, Sn, Pb, Sb, and Bi, preferably Ge, Sn, Pb, Sb, and Bi, more preferably Ge, Sn, Pb, Sb and Bi, most preferably Ge, Sn and Pb, in particular Sn,
each X is independently selected from the group consisting of Al, Si, P, As, S, Se, Te and mixtures thereof, preferably $As^V$, $P^V$, $Si^{IV}$, $Al^{III}$, $S^{VI}$, $Se^{VI}$, $Te^{VI}$, $As^{III}$, $Se^{IV}$, $Te^{IV}$ and mixtures thereof, more preferably $As^V$, $P^V$, $Si^{IV}$, $Al^{III}$, $S^{VI}$ and mixtures thereof, most preferably $As^V$, $P^V$ and mixtures thereof, in particular P, preferably $P^V$, y is a number from 32 to 40, preferably 40 or 32, in particular 40,
m is a number representing the total positive charge m+ of n cations A and the corresponding negative charge m− of the polyanion $[M'M_{12}X_8O_y]$.

According to a second embodiment, the POMs of the present invention are represented by the formula

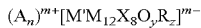

or solvates thereof, wherein
A, n, m, M, M', X and y are the same as defined above,
each R is a substituent group which is covalently bonded to X, and each R is independently selected from the group consisting of a hydrogen atom, a substituent group bonded to X via a carbon atom of said substituent group, a substituent group bonded to X via an oxygen atom of said substituent group, a substituent group bonded to X via a sulfur atom of said substituent group, and a substituent group bonded to X via a nitrogen atom of said substituent group, wherein each R may be the same or different; preferably the substituent group R bonded to X via a carbon atom of said substituent group is selected from the group consisting of alkyl, cycloalkyl, alkenyl, cycloalkenyl, alkynyl, and aryl, wherein each of said substituent groups may be unsubstituted or substituted, and each of said substituent groups optionally may contain one or more heteroatoms resulting in hetero-alkyl, hetero-cycloalkyl, hetero-alkenyl, hetero-cycloalkenyl, hetero-alkynyl, and hetero-aryl, and —$CF_3$, —CN, —$C(O)OR^2$, —$C(O)R^2$, and —$C(O)NR^2R^3$; the substituent group R bonded to X via an oxygen atom of said substituent group is selected from the group consisting of
—$OR^2$, —$O(SO_2)R^2$, —$O(SO)R^2$, —$O(SO_2)OR^2$, —$O(SO)OR^2$, —$OS(O_2)NR^2R^3$, —$OS(O)NR^2R^3$, —$OPO(OR^2)_2$, —$OPO(OR^2)OR^3$, —$OPO(R^2)OR^3$, —$OC(O)R^2$, —$OC(O)NR^2R^3$, and —$OC(O)OR^2$; the substituent group R bonded to X via a sulfur atom of said substituent group is selected from the group consisting of —$SO_3R^2$, —$SR^2$, —$S(O_2)R^2$, —$S(O)R^2$, —$S(O)OR^2$, —$S(O)NR^2R^3$, and —$S(O_2)NR^2R^3$; and the substituent group R bonded to X via a nitrogen atom of said substituent group is selected from the group consisting of
—$NR^2R^3$, —$N(R^2)S(O_2)R^3$, —$N(R^2)S(O_2)NR^3R^4$, —$N(R^2)S(O_2)OR^3$, —$N(R^2)S(O)R^3$, —$N(R^2)S(O)NR^3R^4$, —$N(R^2)S(O)OR^3$, —$N(R^2)PO(OR^3)_2$, —$N(R^2)PO(OR^3)OR^4$, —$N(R^2)PO(R^3)OR^4$, —$N(R^2)C(O)R^3$, —$N(R^2)C(O)OR^3$, —$N(R^2)C(O)NR^3R^4$ and —$NO_2$, wherein $R^2$, $R^3$ and $R^4$ are independently selected from the group consisting of H, alkyl, aryl, alkenyl, alkynyl, hetero-alkyl, hetero-cycloalkyl, hetero-alkenyl, hetero-cycloalkenyl, hetero-alkynyl, hetero-aryl and cycloalkyl; more preferably the substituent group R bonded to X via a carbon atom of said substituent group is selected from the group consisting of alkyl, cycloalkyl, and aryl, wherein each of said substituent groups may be unsubstituted or substituted and each of said substituent groups optionally may contain one or more heteroatoms resulting in hetero-alkyl, hetero-cycloalkyl, and hetero-aryl, and —$CF_3$, —$C(O)OR^2$, and —$C(O)NR^2R^3$; the substituent group R bonded to X via an oxygen atom of said substituent group, is selected from the group consisting of
—$OR^2$, —$O(SO_2)R^2$, —$O(SO_2)OR^2$, —$OS(O_2)NR^2R^3$, —$OPO(OR^2)_2$, —$OC(O)R^2$, —$OC(O)NR^2R^3$, and —$OC(O)OR^2$; the substituent group R bonded to X via a sulfur atom of said substituent group, is selected from the group consisting of
—$SO_3R^2$, —$SR^2$, —$S(O_2)R^2$, and —$S(O_2)NR^2R^3$; and the substituent group R bonded to X via a nitrogen atom of said substituent group is selected from the group consisting of —$NR^2R^3$, —$N(R^2)S(O_2)R^3$, —$N(R^2)S(O_2)NR^3R^4$, —$N(R^2)S(O_2)OR^3$, —$N(R^2)PO(OR^3)_2$, —$N(R^2)C(O)R^3$, —$N(R^2)C(O)OR^3$, and —$N(R^2)C(O)NR^3R^4$, wherein $R^2$, $R^3$ and $R^4$ are independently selected from the group consisting of H, alkyl, aryl, hetero-alkyl, hetero-cycloalkyl, hetero-aryl and cycloalkyl; most preferably the substituent group R bonded to X via a carbon atom of said substituent group is selected from the group consisting of alkyl, and aryl, wherein each of said substituent groups may be unsubstituted or substituted and each of said substituent groups optionally may contain one or more heteroatoms resulting in hetero-alkyl, and hetero-aryl, and —C(O)OR$^2$, and —C(O)NR$^2$R$^3$; the substituent group R bonded to X via an oxygen atom of said substituent group is selected from the group consisting of —OR$^2$, —O(SO$_2$)R$^2$, —OC(O)R$^2$, —OC(O)NR$^2$R$^3$, and —OC(O)OR$^2$; the substituent group R bonded to X via a sulfur atom of said substituent group is selected from the group consisting of —SR$^2$, and —S(O$_2$)R$^2$; and the substituent group R bonded to X via a nitrogen atom of said substituent group is selected from the group consisting of —NR$^2$R$^3$, —N(R$^2$)S(O$_2$)R$^3$, —N(R$^2$)C(O)R$^3$, —N(R$_2$)C(O)OR$_3$, and —N(R$^2$)C(O)NR$^3$R$^4$, wherein $R^2$, $R^3$ and $R^4$ are independently selected from the group consisting of H, alkyl, aryl, hetero-alkyl, and hetero-aryl, and z is a number from 0 to 8, preferably 0 or 8, in particular 0.

According to a third embodiment, the POMs of the present invention are represented by the formula

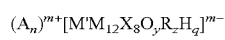

or solvates thereof, wherein

A, n, m, M, M', X, y, R and z are the same as defined above, and q is a number from 0 to 16, preferably 0 to 8, more preferably 0 to 6, most preferably 0.

In one preferred variant of the first, second or third embodiments, all M are the same; preferably wherein all M are the same, and are selected from Pd, Pt, Rh, Ir, and Au, more preferably Pd, Pt and Rh, most preferably Pd and Pt, in particular Pd.

In a second preferred variant of the first, second or third embodiments or of the preferred variant of said embodiments M' is selected from the group of post-transition metals having an oxidation state of +3 or higher, preferably M' is selected from the group of post-transition metals having an oxidation state of +3, +4 or +5, preferably M' is selected from the group of post-transition metals having an oxidation state of +4; in particular M' is selected from the group consisting of Ga$^{III}$, In$^{III}$, Tl$^{III}$, Ge$^{IV}$, Sn$^{IV}$, Pb$^{IV}$, Sb$^{III}$, Sb$^{V}$, Bi$^{III}$ and Bi$^{V}$, preferably M' is selected from the group consisting of Ga$^{III}$, In$^{III}$, Tl$^{III}$, Ge$^{IV}$, Sn$^{IV}$, Pb$^{IV}$, Sb$^{V}$, and Bi$^{V}$, preferably M' is selected from the group consisting of Ge$^{IV}$, Sn$^{IV}$, Pb$^{IV}$, Sb$^{V}$, and BiV, more preferably M' is selected from the group consisting of Ge$^{IV}$, Sn$^{IV}$ and Pb$^{IV}$, most preferably M' is Sn$^{IV}$.

The polyanion [M'M$_{12}$X$_8$O$_y$R$_z$H$_q$] of the POMs according to the invention has been found to show structural analogies to the Keggin anion described above. It comprises twelve noble metal atoms M forming a distorted icosahedron (or distorted cuboctahedron) around the thirteenth central guest atom M'. In contrast to other known POMs in which the framework metal atom geometry is distorted octahedral (or more rarely, tetrahedral, square-pyramidal, or seven-coordinated), the 12 noble metal atoms M have a square-planar coordination sphere. The M cations provide a d$^8$ valence electron configuration. In a preferred embodiment, the large positive charge of the M and M' metal cations is compensated by oxo anions resulting in a M'M$_{12}$O$_{32}$ assembly having approximately cuboctahedral symmetry (e.g., FIG. 2).

In a preferred embodiment, the polyanion [M'M$_{12}$X$_8$O$_y$R$_z$H$_q$] is composed of a classic M'M$_{12}$X$_8$ nanocube, with the central M' being 4 to 8-coordinated, preferably 4, 6 or 8-coordinated, more preferably 4 or 8-coordinated, most preferably 8-coordinated. In a preferred embodiment, the framework of the polyanion [M'M$_{12}$X$_8$O$_y$R$_z$H$_q$] can be divided into three parts (e.g., FIG. 3): the central 8-coordinated M' ion encapsulated in the classic M$_{12}$ cuboctahedron and then surrounded by 0 to 8, preferably 8, X atoms. According to the present invention, none of the X atoms is centrally located. All X atoms are external to the M$_{12}$ cuboctahedron.

In a preferred embodiment, in the solid state, each polyanion is surrounded by n, preferably 1 to 50, more preferably 1 to 30, most preferably 1 to 20 cations A to compensate the charge balance, and those cations, together with optional crystal water molecules, isolate the polyanions from each other.

In a preferred embodiment, where z equals 0, the eight triangular faces of the M'M$_{12}$O$_{32}$ cuboctahedron are each capped by a positively charged XO$_p^{v+}$ group to form a non-protonated distorted cube M'M$_{12}$X$_8$O$_y$ such as M'M$_{12}$X$_8$O$_{40}$. In a preferred embodiment, in the above XO$_p^{v+}$ group, p is 1 if X is As$^V$, P$^V$, Si$^{IV}$, Al$^{III}$, S$^{VI}$, Se$^{VI}$ or Te$^{VI}$. In another preferred embodiment p is 0, if X is a heteroatom having a lone pair of electrons, i.e., X is As$^{III}$, Se$^{IV}$ or Te$^{IV}$. v is the positive charge of the XO$_p^{v+}$ group and is dependent on the oxidation state of X as well as the number of oxygen atoms p. If p is 1, then v is +1 (Al$^{III}$), +2 (Si$^{IV}$), +3 (As$^V$, P$^V$) or +4 (Se$^{VI}$, Te$^{VI}$). If p is 0, then v is equal to the oxidation state of X, such as +3 (As$^{III}$) or +4 (Se$^{IV}$, Te$^{IV}$).

In a preferred embodiment, each of the eight triangular faces of the M'M$_{12}$O$_{32}$ cuboctahedron can also be capped by a positively charged XR$^{t+}$ group to form a non-protonated distorted cube M'M$_{12}$O$_{32}$(XR)$_8$ wherein X is Al, Si, P, As, S, Se, Te, preferably As$^V$, P$^V$, Si$^{IV}$, Al$^{III}$, S$^{VI}$, Se$^{VI}$, Te$^{VI}$, As$^{III}$, Se$^{IV}$, and/or Te$^{IV}$, more preferably As$^V$, P$^V$ and/or Si$^{IV}$ and R is as defined above such as —H, —C$_6$H$_5$, —CH$_3$, —C$_2$H$_5$, —CH$_2$COOH or —CH$_2$NH$_2$. t is the positive charge of the XR$^{t+}$ group and is dependent on the oxidation state of X. In a preferred embodiment, if X is P$^V$ or As$^V$, t is +4 and if X is Si$^{IV}$ t is +3. Group R covalently bonded to the heteroatom allows for tuning of (i) the steric and electrostatic parameters on the surface of the POM, and (ii) the solubility properties of the POM ranging from hydrophilic to hydrophobic. Furthermore, if group R is substituted by one or more X-containing moieties, e.g., —PO$_3$H$_2$, —AsO$_3$H$_2$ or —SiO$_3$H$_3$, a POM polyanion can be linked via such X-containing moieties to one or more other POM polyanions, thus, forming chains or networks of POM polyanions.

In a preferred embodiment, each of the eight triangular faces of the M'M$_{12}$O$_{32}$ cuboctahedron can also be capped by a positively charged X-containing group independently selected from the groups comprising XR$^{t+}$ species and XO$_p^{v+}$ species. In general, if a group R is covalently bonded to X, X is selected preferably from the group consisting of As$^V$, P$^V$ and/or si$^{IV}$.

The POMs of the present invention are in the form of primary and/or secondary particles. In an especially preferred embodiment, the POMs provided by the present invention are mainly in the form of primary particles (i.e. non-agglomerated primary particles), that is at least 90 wt % of the POMs are in the form of primary particles, preferably at least 95 wt %, more preferably at least 99 wt %, in particular substantially all the POMs particles are in the form of primary particles.

The size of the present POMs primary particles has been found to be about 1 nm$^3$ determined by single-crystal X-ray diffraction analysis.

Specific examples of structures of specific POMs of the present invention are also illustrated in FIGS. 2 and 3.

In comparison to known TMSPs (transition metal-substituted POMs), the present POMs are characterized in that at least a major proportion of the metal atom positions of the POM framework are occupied by noble metal atoms selected from Rh, Ir, Pd, Pt, Ag, Au, and mixtures thereof.

Moreover, in contrast to known POMs, the present POMs are further characterized in that they feature one centrally located metal atom position in the POM framework, which position is occupied by a post-transition metal atom selected from Ga, In, Tl, Ge, Sn, Pb, Sb, and Bi. The combination of the one centrally located post-transition metal guest atom and the surrounding noble metal cuboctrahedron provides for POMs having (i) an exceptionally robust polyanion framework and (ii) a unique catalytic performance in reduction reactions. Said unique catalytic performance of the POMs of the present invention stems from (i) the exceptionally high concentration and accessibility of the noble metal centers in the nanosized molecular entity described herein and from (ii) the presence of the centrally located post-transition metal guest atom. While the inventors do not wish to be bound by any particular theory, the presence and nature of the post-transition metal guest atom also impacts the properties of the surrounding noble metal cuboctrahedron, e.g., electronic properties, and thus in particular the catalytic performance of the POMs of the present invention. Hence, the overall properties of the POMs and in particular the catalytic performance in said reduction reactions can be fine-tuned by the specific choice of noble metal(s) in combination with the centrally located post-transition metal guest atom.

In the POMs of the present invention, the cation A can be a Group 1, 2, 3, 4, 5, 6, 7, 8, 9, 10, 11, 12, 13, 14, 15 and 16 metal cation or an organic cation. Preferably, each A is independently selected from the group consisting of cations of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Sb, Te; or phosphonium, ammonium, guanidinium, tetraalkylammonium, protonated aliphatic amines, protonated aromatic amines; or combinations thereof. More preferably, A is selected from lithium, potassium, sodium cations and combinations thereof.

The number n of cations is dependent on the nature of cation(s) A, namely its/their valence, and the negative charge m of the polyanion which has to be balanced. In any case, the overall charge of all cations A is equal to the charge of the polyanion. In turn, the charge m of the polyanion is dependent on the nature and oxidation state of the metals M and M', the nature and oxidation state of the heteroatoms X and the number of oxygen atoms y. Thus, m depends on the oxidation state of the atoms present in the polyanion, e.g., it follows from the oxidation states of O (−2), X (ranging from +3 to +6 such as +3 for Al$^{III}$, As$^{III}$, +4 for Si$^{IV}$, Se$^{IV}$, Te$^{IV}$, +5 for As$^{V}$, P$^{V}$ or +6 Se$^{VI}$ and Te$^{VI}$), and M and M' (normally ranging from +3 to +5 such as +3 for Ga, In and Tl, +4 for Ge, Sb and Pb, and +5 for Sb and Bi). In some embodiments, m ranges from 1 to 45. In particular, m is 6, 9, 10, 12, 14, 22, 30 or 35. In a preferred embodiment, m is 12. Thus, n can generally range from 1 to 45. In particular, n ranges from 6 to 30 and more particularly is 6, 10, 12, 14, 22 or 30. In a preferred embodiment, n is 12.

Generally, A is acting as counterion of the POM and is positioned outside of the polyanion. However, it is also possible that some of the cations A are located within the POM.

In contrast, if one or multiple protons are present as counterion(s) in a preferred embodiment, said one or multiple protons are located within the polyanion, and said one or multiple protons can be covalently bonded to oxygen atom(s) of the polyanion with the proviso that no more than one proton is bonded per oxygen. Thus, each proton being located on a POM and, preferably, being bonded to one or more of the atoms of the polyanion framework, is represented by one of q protons of the polyanion [M'M$_{12}$X$_8$O$_y$R$_z$H$_q$].

Generally, q is ranging from 0 to 16. In particular, q is 0 or 4. In a preferred embodiment q is 0, i.e. no group H is present. In another embodiment q is 1, 2, 3, 4, 5, 6, 7, 8, 9, 10, 11, 12, 13, 14, 15, or 16. In a preferred embodiment of the present invention the q protons are bonded to oxygen atoms of the polyanion framework, with the proviso that each of said protons is bonded to a different oxygen atom of the polyanion framework. Thus, in this specific preferred embodiment the POM is best represented by the formulae

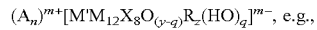

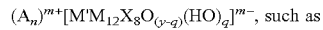

or solvates thereof, wherein A, n, m, M, M', X, y, R, z and q are the same as defined above.

The M atoms have a square-planar coordination sphere, and they provide a d$^8$ valence electron configuration. Preferably M is selected from Pt$^{II}$ or Pd$^{II}$, most preferably M is Pd$^{II}$. In a most preferred embodiment, all M are the same, and all M are Pd$^{II}$ at the same time. Preferably M' is selected from Ge, Sn or Pb, most preferably M' is Sn. In a most preferred embodiment, M' is Sn, especially Sn$^{IV}$. Preferably X is selected from P or As, most preferably X is P. Preferably z and q are 0.

In another embodiment each R is a substituent group which is covalently bonded to X, and R is hydrogen or a substituent group wherein each R that is not hydrogen provides an oxygen atom, a carbon atom, a sulfur atom or a nitrogen atom for coordination to the X atom within the polyanion [M'M$_{12}$X$_8$O$_y$R$_z$H$_q$], wherein each R may be the same or different, preferably R is hydrogen or a substituent group wherein each R that is not hydrogen provides an oxygen atom, a carbon atom, a sulfur atom or a nitrogen atom for coordination to the X atom and wherein each R that is not hydrogen comprises one or more moieties independently selected from the group consisting of H, alkyl, alkenyl, alkynyl, aryl, heteroaryl, cycloalkyl, heterocycloalkyl, aryalkyl, arylalkenyl, cycloalkylalkyl, heterocycloalkylalkyl and heteroarylalkyl, wherein each of said alkyl, alkenyl, alkynyl, aryl, heteroaryl, cycloalkyl and heterocycloalkyl can be unsubstituted or substituted with one or more moieties which can be the same or different, each of said moieties being independently selected from the group consisting of halogen, alkyl, alkenyl, alkynyl, aryl, heteroaryl, cycloalkyl, heterocycloalkyl, arylalkyl, arylalkenyl, cycloalkylalkyl, heterocycloalkylalkyl, heteroarylalkyl, —CF$_3$, —CN, —OR$^2$, —NR$^2$R$^3$, —C(O)OR$^2$, —C(O) R, —C(O)NR$^2$R$^3$, —SO$_3$H, —SR$^2$, —S(O$_2$)R$^2$, —S(O$_2$) NR$^2$R$^3$, —N(R$^2$)S(O$_2$)R$^3$, —N(R$^2$)C(O)R$^3$, —N(R$^2$)C(O)

NR$^2$R$^3$, —NO$_2$, and X-containing moieties through which a POM can be linked to one or more other POMs, each of R$^2$ and R$^3$ being selected from the group consisting of H, alkyl, aryl, alkenyl, alkynyl, hetero-alkyl, hetero-cycloalkyl, hetero-alkenyl, hetero-cycloalkenyl, hetero-alkynyl, hetero-aryl and cycloalkyl.

In general, R is hydrogen or an unsubstituted or substituted group, preferably an unsubstituted or substituted organic group, as defined in this specification. As used herein, "alkyl" represents a straight or branched aliphatic hydrocarbon group with 1 to about 20 carbon atoms. Preferred alkyl groups contain 1 to about 12 carbon atoms. More preferred alkyl groups contain 1 to about 6 carbon atoms. Non-limiting examples of suitable alkyl groups include methyl, ethyl, n-propyl, isopropyl and t-butyl. "Alkenyl" represents a straight or branched aliphatic hydrocarbon group containing at least one carbon-carbon double bond and having 2 to about 15 carbon atoms. Preferred alkenyl groups have 2 to about 12 carbon atoms; and more preferably 2 to about 4 carbon atoms. Non-limiting examples of suitable alkenyl groups include ethenyl, propenyl and 2-butenyl. "Alkynyl" represents a straight or branched aliphatic hydrocarbon group containing at least one carbon-carbon triple bond and having 2 to about 15 carbon atoms. Preferred alkynyl groups have 2 to about 12 carbon atoms; and more preferably 2 to about 4 carbon atoms in the chain. Non-limiting examples of suitable alkynyl groups include ethynyl, propynyl, 2-butynyl and 3-methylbutynyl. "Aryl" represents an aromatic monocyclic or multicyclic ring system comprising about 6 to about 14 carbon atoms, preferably about 6 to about 10 carbon atoms. Non-limiting examples of suitable aryl groups include phenyl and naphthyl. "Heteroaryl" represents an aromatic monocyclic or multicyclic ring system comprising about 5 to about 14 ring atoms, preferably about 5 to about 10 ring atoms, in which one or more of the ring atoms is an element other than carbon, for example, nitrogen, oxygen or sulfur, alone or in combination. Preferred heteroaryls contain about 5 to about 6 ring atoms.

Non-limiting examples of suitable heteroaryls include pyridyl, pyrazinyl, furanyl, thienyl, pyrimidinyl, pyridine (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo [2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. "Cycloalkyl" represents a non-aromatic mono- or multicyclic ring system comprising 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like. "Heterocyclyl" represents a non-aromatic saturated monocyclic or multicyclic ring system comprising 3 to about 10 ring atoms, preferably about 5 to about 10 ring atoms, in which one or more of the atoms in the ring system is an element other than carbon, for example, nitrogen, oxygen or sulfur, alone or in combination. Preferred heterocyclyls contain about 5 to about 6 ring atoms. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Arylalkyl" represents an arylalkyl-group in which the aryl and alkyl are as previously described. Non-limiting examples of suitable arylalkyl groups include benzyl, 2-phenethyl and naphthalenylmethyl. The bond to X is through the alkyl. Likewise, also "cycloalkylalkyl", "heterocyclylalkyl" and "heteroarylalkyl" are bound to X via the alkyl. In preferred embodiments, R is H, —CH$_3$, —C$_2$H$_5$, —C$_3$H$_7$, —C$_4$H$_9$, —C$_6$H$_5$, —CH$_2$COOH, —CH$_2$NH$_2$, —CH$_2$CH$_2$COOH, —CH$_2$CH$_2$Cl, —CH$_2$CH$_2$CH(NH$_2$)COOH, -(p-C$_6$H$_4$NH$_2$), -(p-C$_6$H$_4$NO$_2$), -(p-C$_6$H$_4$OH) or 3-nitro-4-hydroxyphenyl.

Generally, z is ranging from 0 to 8. In particular, z is 0 or 8. In a preferred embodiment z is 0, i.e. no group R is present. In another embodiment z is 1, 2, 3, 4, 5, 6, 7, or 8.

The number of oxygen atoms y depends on the nature of the heteroatoms X and the number z of groups R present in the POM. In a preferred embodiment, if z is 0 and X is As$^V$, P$^V$, Si$^{IV}$, Al$^{III}$, S$^{VI}$, Se$^{VI}$ or Te$^{VI}$ then y is 40. In another preferred embodiment, if z is 0 and X is As$^{III}$, Se$^{IV}$ or Te$^{IV}$, then y is 32. In another preferred embodiment, if z is 8, then X is preferably As$^V$, P$^V$ and Si$^{IV}$ and y is 32.

Thus, in a preferred embodiment the invention relates to a POM $(A_n)^{m+}[M'M_{12}X_8O_yR_zH_q]^{m-}$, wherein M' is Sn.

Thus, in a preferred embodiment the invention relates to a POM $(A_n)^{m+}[M'M_{12}X_8O_yR_zH_q]^{m-}$, wherein M is Pd$^{II}$, M' is Sn and X is P.

Thus, in a preferred embodiment the invention relates to a POM $(A_n)^{m+}[M'M_{12}X_8O_yR_zH_q]^{m-}$, wherein M is Pd$^{II}$, M' is Sn and X is P, wherein all M are the same.

Thus, in a preferred embodiment the invention relates to a POM $(A_n)^{m+}[M'M_{12}X_8O_yR_zH_q]^{m-}$, wherein M is Pd$^{II}$, M' is Sn$^{IV}$, X is P, and z is 0.

Accordingly, in a preferred embodiment the invention relates to POMs represented by the formula $(A_n)^{12+}[SnPd_{12}P_8O_{40}]^{12-}$ or solvates thereof, wherein A and n are the same as defined above.

Further, suitable examples of POMs according to the invention are represented by the formulae $(A_n)^{m+}[M'M_{12}X_8O_yR_zH_q]^{m-}$, e.g., $(A_n)^{m+}[M'M_{12}X_8O_yH_q]^{m-}$, $(A_n)^{m+}[M'M_{12}X_8O_yR_z]^{m-}$, $(A_n)^{m+}[M'M_{12}X_8O_y]^{m-}$, $(A_n)^{m+}[M'Pd_{12}X_8O_yR_zH_q]^{m-}$, $(A_n)^{m+}[M'Pd_{12}X_8O_y]^{m-}$, $(A_n)^{m+}[M'Pd_{12}X_8O_{40}]^{m-}$, $(A_n)^{12+}[M'Pd_{12}X_8O_{40}]^{12-}$, or $(A_n)^{8+}[M'Pd_{12}X_8O_{36}(HO)_4]^{8-}$, $(A_{13})^{12+}[M'Pd_{12}X_8O_{40}]^{12-}$, $(A_n)^{m+}[SnPd_{12}X_8O_yR_zH_q]^{m-}$, such as $(A_n)^{m+}[SnPd_{12}X_8O_y]^{m-}$, $(A_n)^{m+}[SnPd_{12}X_8O_{40}]^{m-}$, $(A_n)^{12+}[SnPd_{12}X_8O_{40}]^{12-}$, or $(A_n)^{8+}[SnPd_{12}X_8O_{36}(HO)_4]^{8-}$, $(A_{12})^{12+}[SnPd_{12}X_8O_{40}]^{12-}$, $(A_n)^{m+}[SnPt_{12}X_8O_yR_zH_q]^{m-}$, such as $(A_n)^{m+}[SnPt_{12}X_8O_y]^{m-}$, $(A_n)^{m+}[SnPt_{12}X_8O_{40}]^{m-}$, $(A_n)^{12+}[SnPt_{12}X_8O_{40}]^{12-}$, or $(A_n)^{8+}[SnPt_{12}X_8O_{36}(HO)_4]^{8-}$, $(A_{12})^{12+}[SnPt_{12}X_8O_{40}]^{12-}$, $(A_n)^{m+}[GePd_{12}X_8O_yR_zH_q]^{m-}$, such as $(A_n)^{m+}[GePd_{12}X_8O_y]^{m-}$, $(A_n)^{m+}[SnPd_{12}X_8O_{40}]^{m-}$, $(A_n)^{12+}[GePd_{12}X_8O_{40}]^{12-}$, or $(A_n)^{8+}[GePd_{12}X_8O_{36}(HO)_4]^{8-}$, $(A_{12})^{12+}[GePd_{12}X_8O_{40}]^{12-}$, $(A_n)^{m+}[M'Pd_{12}X_8O_yR_zH_q]^{m-}$, such as $(A_n)^{m+}[M'Pd_{12}X_8O_y]^{m-}$, $(A_n)^{m+}[M'Pd_{12}X_8O_{40}]^{m-}$, $(A_n)^{12+}[M'Pd_{12}X_8O_{40}]^{12-}$, or $(A_n)^{8+}[M'Pd_{12}P_8O_{36}(HO)_4]^{8-}$, $(A_{12})^{12+}[M'Pd_{12}P_8O_{40}]^{12-}$, $(A_n)^{m+}[SnM_{12}P_8O_yR_zH_q]^{m-}$, such as $(A_n)^{m+}[SnM_{12}P_8O_y]^{m-}$, $(A_n)^{m+}[SnM_{12}P_8O_{40}]^{m-}$, $(A_n)^{12+}[SnM_{12}P_8O_{40}]^{12-}$, or $(A_n)^{8+}[SnM_{12}P_8O_{36}(HO)_4]^{8-}$, $(A_{12})^{12+}[SnM_{12}P_8O_{40}]^{12-}$, $(Na_{12})^{12+}[M'Pd_{12}P_8O_{40}]^{12-}$, or $(Na_8)^{8+}[M'Pd_{12}P_8O_{36}(OH)_4]^{8-}$, $(A_n)^{12+}[M'Pt_{12}P_8O_{40}]^{12-}$, or $(A_n)^{8+}[M'Pt_{12}P_8O_{36}(HO)_4]^{8-}$, $(A_n)^{12+}[M'Pd_{12}As_8O_{40}]^{12-}$, or $(A_n)^{8+}[M'Pd_{12}As_8O_{36}(HO)_4]^{8-}$, $(A_{12})^{12+}[M'Pt_{12}P_8O_{40}]^{12-}$, or $(A_8)^{8+}[M'Pt_{12}P_8O_{36}(HO)_4]^{8-}$, $(A_{12})^{12+}[M'Pd_{12}As_8O_{40}]^{12-}$, or $(A_8)^{8+}[M'Pd_{12}As_8O_{36}(HO)_4]^{8-}$, and $(A_{12})^{12+}[SnPd_{12}P_8O_{40}]^{12-}$, such as $(Na_{12})^{12+}[SnPd_{12}P_8O_{40}]^{12-}$, or $(A_8)^{8+}[SnPd_{12}P_8O_{36}(HO)_4]^{8-}$, such as $(Na_8)^{8+}[SnPd_{12}P_8O_{36}(HO)_4]^{8-}$, $(A_{12})^{12+}[SnPd_{12}P_8O_{40}]^{12-}$, such as $(Na_{12})^{12+}[SnPd_{12}P_8O_{40}]^{12-}$, or $(A_8)^{8+}[SnPd_{12}P_8O_{36}(HO)_4]^{8-}$, such as $(Na_8)^{8+}[SnPd_{12}P_8O_{36}(HO)_4]^{8-}$, $(A_{12})^{12+}[SnPd_{12}As_8O_{40}]^{12-}$, such as $(Na_{12})^{12+}[SnPd_{12}As_8O_{40}]^{12-}$, or $(A_8)^{8+}[SnPd_{12}As_8O_{36}(HO)_4]^{8-}$, such as $(Na_8)^{8+}[SnPd_{12}As_8O_{36}(HO)_4]^{8-}$, $(A_{12})^{12+}[SnPt_{12}As_8O_{40}]^{12-}$, such as $(Na_{12})^{12+}[SnPt_{12}As_8O_{40}]^{12-}$, or $(A_8)^{8+}[SnPt_{12}As_8O_{36}(HO)_4]^{8-}$, such as $(Na_8)^{8+}[SnPt_{12}As_8O_{36}(HO)_4]^{8-}$, The invention also includes solvates of the present POMs. A solvate is an association of solvent molecules with a POM. Preferably, water is associated with the POMs and thus, the POMs according to the invention can in particular be represented by the formulae $(A_n)^{m+}[M'M_{12}X_8O_yR_zH_q]^{m-} \cdot wH_2O$, e.g., $(A_n)^{m+}[M'M_{12}X_8O_y]^{m-} \cdot wH_2O$, $(A_n)^{m+}[M'M_{12}X_8O_{40}]^{m-} \cdot wH_2O$, or $(A_n)^{m+}[M'M_{12}X_8O_{(40-q)}(HO)_q]^{m-} \cdot wH_2O$ and $(A_n)^{m+}[M'Pd_{12}X_8O_{(40-q)}(HO)_q]^{m-} \cdot wH_2O$, wherein A, n, m, M, M', X, y, R, z and q are the same as defined above, and w represents the number of attracted water molecules per POM and mostly depends on the type of cations A. In some embodiments w is an integer from 1 to 100, preferably 1 to 80, more preferably 10 to 60, most preferably 20 to 50 such as 43.

Suitable examples of the POM solvates according to the invention are represented by the formulae $(A_n)^{m+}[M'Pd_{12}X_8O_{40}]^{m-} \cdot wH_2O$, or $(A_n)^{m+}[M'Pt_{12}X_8O_{40}]^{m-} \cdot wH_2O$, e.g.

$(A_n)^{m+}[M'Pd_{12}X_8O_{40}]^{m-} \cdot wH_2O$, $(A_n)^{m+}[M'Pd_{12}As_8O_{40}]^{m-} \cdot wH_2O$, $(A_n)^{m+}[SnPd_{12}X_8O_{40}]^{m-} \cdot wH_2O$, $(A_n)^{m+}[SnPd_{12}P_8O_{40}]^{m-} \cdot wH_2O$, $(A_n)^{m+}[SnPd_{12}As_8O_{40}]^{m-} \cdot wH_2O$, $(A_n)^{12+}[SnPd_{12}P_8O_{40}]^{12-} \cdot wH_2O$, such as $(Na_{12})^{12+}[SnPd_{12}P_8O_{40}]^{12-} \cdot 43H_2O$, $(A_n)^{12+}[SnPd_{12}As_8O_{40}]^{12-} \cdot wH_2O$, such as $(Na_{12})^{12+}[SnPd_{12}As_8O_{40}]^{12-} \cdot 43H_2O$, $(A_n)^{m+}[M'M_{12}X_8O_{(y-q)}]^{m-} \cdot wH_2O$, and $(A_n)^{m+}[M'M_{12}X_8O_{(40-q)}]^{m-} \cdot wH_2O$, such as $(A_n)^{m+}[SnM_{12}P_8O_{(y-q)}(HO)_q]^{m-} \cdot wH_2O$, and $(A_n)^{m+}[M'Pd_{12}P_8O_{36}(HO)_4]^{m-} \cdot 43H_2O$, e.g.

$(A_n)^{m+}[SnPd_{12}P_8O_{36}(HO)_4]^{m-} \cdot wH_2O$, $(A_n)^{8+}[SnPd_{12}P_8O_{36}(HO)_4]^{8-} \cdot 43H_2O$, such as $(Na_8)^{8+}[SnPd_{12}P_8O_{36}(HO)_4]^{8-} \cdot 43H_2O$.

In a preferred embodiment, water molecules, if present at all, are coordinated to protons and/or A cations, while the M and M' cations are not coordinated by water. In a preferred embodiment, a proportion of the water molecules is not directly attached to the POM framework $(A_n)^{m+}[M'M_{12}X_8O_yR_zH_q]^{m-}$ by coordination but rather indirectly by hydrogen-bonding as water of crystallization. Thus, in a preferred embodiment, the attracted water molecules, if present at all, are coordinated to A cations and/or possibly exhibit weak interactions by hydrogen bonding to protons of the POM and/or the attracted water molecules, if present at all, are water of crystallization.

The guest atom M' cannot be replaced or removed without destroying the structural framework of the polyanion, once the polyanion framework is formed.

In another embodiment, the POMs may be further calcined at a temperature not exceeding the transformation temperature of the POM, i.e. the temperature at which decomposition of the POM starts to take place (usually about 600-700° C. for the present POMs according to their corresponding TGA). Thus, in a preferred embodiment the POMs of the present invention are thermally stable up to temperatures of around 600-700° C. For the calcination, common equipment may be used, that is commercially available. Calcination of the POMs may be conducted under an oxygen containing gas such as air, under vacuum, under hydrogen or under an inert gas such as argon or nitrogen, more preferably under inert gas, most preferably under nitrogen. Calcination may help to activate a POM pre-catalyst by forming active sites. Upon heating, POM salts first loose water molecules (of water of crystallization) and then organic groups (if present) before they start to transform/decompose, e.g. by oxidation. TGA can be used to study the weight loss of the POM salts, and Differential Scanning calorimetry (DSC) indicates if each step is endo- or exothermic. Such measurements may be carried out e.g. under nitrogen gas, air, oxygen or hydrogen.

In many cases, however, and in particular if the POM is used as a catalyst or pre-catalyst under reductive conditions, drying of the POM without calcination may be sufficient.

The invention is further directed to a process for preparing POMs according to the invention.

A process for preparing POMs according to the present invention comprises:
(a) reacting at least one source of M and at least one source of M' with at least one X-containing and optionally R-containing starting material to form a salt of the polyanion $[M'M_{12}X_8O_yR_zH_q]$ or a solvate thereof,
(b) optionally adding at least one salt of A to the reaction mixture of step (a) to form a POM of formula $(A_n)^{m+}[M'M_{12}X_8O_yR_zH_q]^{m-}$ or a solvate thereof, and
(c) recovering the POM or solvate thereof,
wherein A, n, m, M, M', X, y, R, z and q are the same as defined above.

In step (a) of said process at least one source of M' is used, especially one source of M'. Generally, in a preferred embodiment of the present invention, salts of the following metals Ga, In, Tl, Ge, Sn, Pb, Sb, and Bi such as chlorides, fluorides, hydroxides, nitrates, acetates and/or sulfates can be used as source for M'. More preferably, if M' is Sn, $SnCl_4$, $Sn(CH_3COO)_4$, $SnBr_4$, and/or $Sn(NO_3)_4$ are used; if M' is Ge, $GeCl_4$ is used; if M' is Pb, $PbCl_4$ and/or $Pb(CH_3COO)_4$ are used; if M' is Bi, $BiCl_3$, $Bi(NO_3)_3$ and/or $BiBr_3$ are used; if M' is Sb, $SbCl_5$ and/or $Sb(CH_3COO)_3$ are used. More preferably, M' is Sn and the Sn source is $SnCl_4$.

In step (a) of said process at least one source of M is used, especially one source of M. Generally, in a preferred embodiment of the present invention, $Pd^{II}$ salts such as $PdCl_2$, $Pd(NO_3)_2$, $Pd(CH_3COO)_2$ and $PdSO_4$; $Pt^{II}$ salts such as $PtCl_2$; $Rh^I$ salts such as $[(C_6H_5)_3P]_2RhCl(CO)$ and $[Rh(CO)_2Cl]_2$; $Ir^I$ salts such as $[C_6H_5)_3P]_2IrCl(CO)$; $Au^{III}$ salts such as $AuCl_3$, $Au(OH)_3$ and $HAuCl_4$.aq; and $Ag^{III}$ salts preferably generated with oxidizing reagents from $Ag^I$ salts such as $AgNO_3$, $AgF$ and $AgCl$ can be used as source for the noble metal M atoms. More preferably, the $Pd^{II}$ source is $PdCl_2$ or $Pd(CH_3COO)_2$ and the $Pt^{II}$ source is $PtCl_2$.

In step (a) of said process the metal source or metal sources are reacted with at least one X-containing starting material. For instance, an oxide of X or an oxo acid of X may be used as X-containing starting material. It is also possible to use a water-soluble salt such as a halide of X. In one embodiment of the present invention, suitable examples of X-containing starting materials include $X_2O_5$ such as $As_2O_5$ or $P_2O_5$; $X_2O_3$ such as $As_2O_3$; $H_3PO_4$, $H_3PO_3$, $H_2SeO_3$, $H_2SeO_4$, $H_2TeO_3$, $H_2TeO_4$, $H_2SO_4$, $H_4SiO_4$, $Na_4SiO_4$ and $AlCl_3$. In a preferred embodiment of the present invention the X-containing starting material is any salt or derivative of $PO_4^{3-}$, such as $H_3PO_4$, $NaH_2PO_4$, $Na_2HPO_4$, $Na_3PO_4$, $KH_2PO_4$, $K_2HPO_4$, $K_3PO_4$, $NaKHPO_4$, $NaK_2PO_4$, $Na_2KPO_4$ or mixtures thereof, preferably $H_3PO_4$, $NaH_2PO_4$, $Na_2HPO_4$, $Na_3PO_4$, or mixtures thereof, and most preferably $NaH_2PO_4$, $Na_2HPO_4$ or mixtures thereof, in particular $NaH_2PO_4$. In an especially preferred embodiment, the noble metal M source, preferably $Pd(CH_3COO)_2$, is reacted with $NaH_2PO_4$. In a further preferred embodiment, the noble metal M source, preferably $Pd(CH_3COO)_2$, and the source of M', preferably $SnCl_4$, are reacted with $NaH_2PO_4$.

If the resulting POM is to contain one or more groups R, the X-containing starting material also contains R. In particular, an X-containing starting material is used in which R is covalently bound to X. For example, R-containing derivatives of phosphonic acid, arsonic acid and trichlorosilane can be used. In a preferred embodiment of the present invention examples of suitable XR-containing starting materials include methylphosphonic acid, phosphonoacetic acid, 2-carboxyethylphosphonic acid, phenylphosphonic acid, methylarsonic acid, ethylarsonic acid, propylarsonic acid, butylarsonic acid, p-arsanilic acid, DL-2-amino-4-arsonobutanoic acid monohydrate, p-aminophenylarsonic acid, ammonium 4-nitrophenylarsonate, ammonium-4-hydroxyphenyl-arsonic acid chloride dihydrate, 3-nitro-4-hydroxyphenylarsonic acid, 4-hydroxyphenylarsonic acid, methyltrichlorosilane, ethyltrichlorosilane, O-chloroethyltrichlorosilane and phenyltrichlorosilane. In order to link a POM with at least one other POM, R can be substituted with at least one further X-containing moiety. In another preferred embodiment of the present invention, examples of X—R—X-containing starting materials which can be used in step (a) of said process include methylenediphosphonic acid, 1,2-ethylene-diphosphonic acid, 2-hydroxypropane-1, 3-bis (arsonic acid), 1R(S),2S(R)-1,2-bis(tri-chlorosilyl)-1, 2-diphenylethane, 1,3-bis (trichlorosilylmethyl)benzene, 1,4-bis (trichlorosilyl-methyl)benzene and 1,1,1,4,4,4-hexachloro-1,4-disilabutane. In another preferred embodiment of the present invention suitable examples of X-containing starting materials which comprise more than two X moieties include nitrilotris(methylphosphonic acid) and hexakis(3-(trichlorosilyl)propyl)benzene. Most preferably, the X-containing starting material which also contains one or more R is water-soluble.

In a preferred embodiment, step (a) of said process is carried out in an aqueous solution. If the X-containing starting material has only a low solubility in water (for example, because it also contains one or more groups R) it is possible to dissolve the X-containing starting material in a small volume of organic solvent and then adding this solution to an aqueous solution of the sources of M and M' or vice versa. Examples of suitable organic solvents include, but are not limited to acetonitrile, acetone, toluene, DMF, DMSO, ethanol, methanol, n-butanol, sec-butanol, isobutanol and mixtures thereof. It is also possible to use emulsifying agents to allow the reagents of step (a) of said process to undergo a reaction.

Furthermore, in a preferred embodiment of the present invention, in step (a) of said process, the concentration of the noble metal ions originating from the at least one source of M ranges from 0.005 to 5 mole/l, preferably from 0.01 to 1 mole/l, more preferably from 0.01 to 0.1 mole/l, the concentration of the metal ions originating from the at least one source of M' ranges from 0.0005 to 0.5 mole/l, preferably 0.001 to 0.1 mole/l, more preferably 0.005 to 0.05 mole/l, and the concentration of the at least one X-containing starting material ranges from 0.0005 to 5 mole/l, preferably 0.001 to 1 mole/l, more preferably 0.005 to 0.75 mole/l, with the proviso that the ratio of the molar concentration of the metal ions originating from the at least one source of M' to the molar concentration of the metal ions originating from the at least one source of M is in the range from 0.1 to 50, preferably from 1 to 20, more preferably from 1 to 10.

Furthermore, in a preferred embodiment, the pH of the aqueous solution in step (a) of said process ranges from 2 to 14, preferably from 4 to 12 and more preferably from 6 to 11.

Most preferably, the pH is from about 7 to about 10, for instance from about 7.5 to about 9.5. Generally, in a preferred embodiment of the present invention a buffer solution can be used for maintaining the pH value in a certain range.

In a preferred embodiment of the present invention the buffer is a phosphate or acetate buffer or a mixture thereof and preferably said phosphate or acetate buffer is derived from $H_3PO_4$, $NaH_2PO_4$, $Na_2HPO_4$, $Na_3PO_4$, $KH_2PO_4$, $K_2HPO_4$, $K_3PO_4$, $NaKHPO_4$, $NaK_2PO_4$, $Na_2KPO_4$, $Na(CH_3CO_2)$, $K(CH_3CO_2)$, $Mg(CH_3CO_2)_2$, $Ca(CH_3CO_2)_2$, $CH_3CO_2H$ or mixtures thereof, preferably $H_3PO_4$, $NaH_2PO_4$, $Na_2HPO_4$, $Na_3PO_4$, $Na(CH_3CO_2)$, $K(CH_3CO_2)$, $CH_3CO_2H$ or mixtures thereof, and most preferably $NaH_2PO_4$, $Na_2HPO_4$, $Na(CH_3CO_2)$, $K(CH_3CO_2)$ or mixtures thereof, in particular $NaH_2PO_4$, $Na(CH_3CO_2)$ or mixtures thereof. It is more preferred to have either a phosphate or an acetate buffer, whereas it is less preferred to have a mixture of phosphate and acetate buffer. In a preferred embodiment of the present invention said phosphate buffer is preferably derived from $NaH_2PO_4$, whereas said acetate buffer is preferably derived from $Na(CH_3CO_2)$. In a very preferred embodiment of the present invention the buffer is a phosphate buffer, most preferably derived from $NaH_2PO_4$.

Generally, in a preferred embodiment of the present invention, additional base or acid solution can be used for adjusting the pH to a certain value. It is particularly preferred to use aqueous sodium hydroxide or $H_2SO_4$ solution having a concentration of 1 M. In another embodiment, the concentration of the aqueous base or acid solution (preferably aqueous sodium hydroxide or $H_2SO_4$ solution) is from 0.1 to 12 M, preferably 0.2 to 8 M, more preferably from 0.5 to 6 M, most preferably about 1 M. Generally, in a very preferred embodiment of the present invention additional base solution can be used for adjusting the pH to a certain pH value. It is particularly preferred to use aqueous sodium hydroxide solution having a concentration of 1 M. In another embodiment, the concentration of the aqueous base solution (preferably aqueous sodium hydroxide solution) is from 0.1 to 12 M, preferably 0.2 to 8 M, more preferably from 0.5 to 6 M, most preferably about 1 M.

In the context of the present invention the pH of the aqueous solution in step (a) of said process refers to the pH as measured at the end of the reaction. In the preferred embodiment where e.g. an aqueous sodium hydroxide solution is used for adjusting the pH-value, the pH is measured after the adjustment at the end of the reaction. pH values are at 20° C., and are determined to an accuracy of ±0.05 in accordance with the IUPAC Recommendations 2002 (R. P. Buck et al., Pure Appl. Chem., Vol. 74, No. 11, pp. 2169-2200, 2002).

A suitable and commercially available instrument for pH measurement is the Mettler Toledo FE20 pH meter. The pH calibration is carried out as 2-point calibration using a pH=4.01 standard buffer solution and a pH=7.00 standard buffer solution. The resolutions are: 0.01 pH; 1 mV; and 0.1° C. The limits of error are: ±0.01 pH; ±1 mV; and ±0.5° C.

A very preferred embodiment of the present invention is said process, wherein in step (a) the at least one source of M, the at least one source of M', the at least one source of X-containing and optionally the at least one source of R-containing starting material are dissolved in a solution of phosphate buffer derived from $NaH_2PO_4$, preferably an 0.1 to 1.0 M phosphate buffer solution derived from $NaH_2PO_4$, in particular a 0.25 to 0.75 M phosphate buffer solution derived from $NaH_2PO_4$, and most preferred a 0.5 M phosphate buffer solution derived from $NaH_2PO_4$.

Another very preferred embodiment of the present invention is said process, wherein in step (a) the buffer already comprises the X-containing starting material. In this embodiment the buffer is most preferably a phosphate buffer, wherein said phosphate buffer is derived preferably from $H_3PO_4$, $NaH_2PO_4$, $Na_2HPO_4$, $Na_3PO_4$, $KH_2PO_4$, $K_2HPO_4$, $K_3PO_4$, $NaKHPO_4$, $NaK_2PO_4$, $Na_2KPO_4$ or mixtures thereof, more preferably from $H_3PO_4$, $NaH_2PO_4$, $Na_2HPO_4$, $Na_3PO_4$, or mixtures thereof, and most preferably from $NaH_2PO_4$, $Na_2HPO_4$, or mixtures thereof, in particular from $NaH_2PO_4$.

In step (a) of the process of the present invention, the reaction mixture is typically heated to a temperature of from 20° C. to 100° C., preferably from 50° C. to 90° C., preferably from 70° C. to 80° C., preferably from 75° C. to 80° C., and most preferably about 80° C.

In step (a) of the process of the present invention, the reaction mixture is typically heated for about 10 min to about 4 h, more preferably for about 30 min to 2 h, most preferably for about 90 min Further, it is preferred that the reaction mixture is stirred during step (a).

With regard to the present invention the term crude mixture relates to an unpurified mixture after a reaction step and is thereby used synonymously with reaction mixture of the preceding reaction step.

In a preferred embodiment of the process of the present invention, between step (a) and (b), the crude mixture is filtered. Preferably, the crude mixture is filtered immediately after the end of step (a), i.e. immediately after the stirring is turned off, and is then optionally cooled. Alternatively, if applicable the heated crude mixture is cooled first, preferably to room temperature, and subsequently filtered. The purpose of this filtration is to remove solid impurities after step (a). Thus, the product of step (a) remains in the filtrate.

In a preferred embodiment, in case cation A is not present in the crude mixture or filtrate already, or the concentration of A in the crude mixture or filtrate should be increased, in step (b) of the process, a salt of the cation A can be added to the reaction mixture of step (a) of the process or to its corresponding filtrates to form $(A_n)^{m+}[M'M_{12}X_8O_yR_zH_q]^{m-}$. Preferably, the salt of A is added as a solid or in the form of an aqueous solution. The counterions of A can be selected from the group consisting of any stable, non-reducing, water-soluble anion, e.g., halides, nitrate, sulfate, acetate, phosphate. Preferably, the acetate or phosphate salt is used. However, the addition of extra cations A in step (b) of the process is not necessary if the desired cations are already present during step (a) of the process, for example, as a component of the buffer preferably used as solvent in step (a) of the process or a component of any of the sources of X, M and/or M' including, for example, palladium and platinum cations themselves. Preferably, all desired cations are already present during step (a) of the process, thus, that there is no optional addition of extra cations necessary.

In step (c) of the process of the present invention, the POMs according to the invention or solvate thereof, formed in step (a) or (b) of said process, are recovered. For example, isolation of the POMs or solvate thereof can be effected by common techniques including bulk precipitation or crystallization. In a preferred embodiment of the present invention the POMs are isolated as crystalline or amorphous solids, preferably as crystalline solids. Crystallization or precipitation can be effected by common techniques such as evaporation or partial evaporation of the solvent, cooling, change of solvent, solvents or solvent mixtures, addition of crystallization seeds, etc. In a preferred embodiment the addition of cation A in step (b) of the process can induce crystallization or precipitation of the desired POM $(A_n)^{m+}[M'M_{12}X_8O_yR_zH_q]^{m-}$, wherein fractional crystallization is preferable. In a preferred embodiment, fractional crystallization might be accomplished by the slow addition of a specific amount of cation A to the reaction mixture of step (a) of the process or to its corresponding filtrates which might be beneficial for product purity and yield.

A preferred embodiment of the present invention is such a process wherein water is used as solvent, the at least one source of M is a water-soluble salt of $Pt^{II}$ or $Pd^{II}$, preferably selected from $PtCl_2$, $Pd(CH_3COO)_2$, $PdCl_2$, $Pd(NO_3)_2$ or $PdSO_4$, in particular a salt of $Pd^{II}$ selected from $Pd(CH_3COO)_2$, $PdCl_2$, $Pd(NO_3)_2$ or $PdSO_4$, such as $Pd(CH_3COO)_2$ or $PdCl_2$; the at least one source of M' is a water-soluble germanium or tin salt, preferably germanium (IV) chloride or tin(IV) chloride, in particular a water-soluble tin salt, preferably tin(IV) chloride; and the at least one source of X is an oxide of X or any salt or derivative of $PO_4^{3-}$, preferably $As_2O_3$, $As_2O_5$, $P_2O_5$ or a salt of $PO_4^3$ in particular $NaH_2PO_4$.

A very preferred embodiment of the present invention is such a process wherein water is used as solvent, the at least one source of M is a water-soluble salt of $Pd^{II}$, preferably palladium nitrate, palladium sulfate, palladium chloride or palladium acetate, the at least one source of M' is a water-soluble tin salt, preferably tin(IV) chloride, and the at least one source of X is any salt or derivative of $PO_4^{3-}$, in particular $NaH_2PO_4$.

A most preferred embodiment of the present invention is a process wherein in step (a) at least one source of M is used and all M are the same, preferably wherein all M are Pd.

According to one embodiment, the present POMs can be immobilized on a solid support. The present invention thus also relates to supported POMs comprising the POMs of the present invention or prepared by the process of the present invention on a solid support. Suitable supports include but are not limited to materials having a high surface area and/or a pore size which is sufficient to allow the POMs to be loaded, e.g., polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous materials, like mesoporous silica, such as SBA-15 and MCM-41, zeolites, aluminophosphates (ALPOs), silicoaluminophosphates (SAPOs), metal organic frameworks (MOFs), zeolitic imidazolate frameworks (ZIFs), periodic mesoporous organosilicas (PMOs), and mixtures thereof and modified compounds thereof. Preferred supports are, for instance, mesoporous silica, more preferably SBA-15 or MCM-41, most preferably SBA-15. A variety of such solid supports is commercially available or can be prepared by common techniques. Furthermore, there are various common techniques to modify or functionalize solid supports, for example with regard to the size and shape of the surface or the atoms or groups available for bonding on the surface.

In a preferred embodiment of the present invention the immobilization of the POMs to the surface of the solid support is accomplished by means of adsorption, including physisorption and chemisorption, preferably physisorption. The adsorption is based on interactions between the POMs and the surface of the solid support such as van-der-Waals interactions, hydrogen-bonding interactions, ionic interactions, etc.

In a preferred embodiment the negatively charged polyanions $[M'M_{12}X_8O_yR_zH_q]$ are adsorbed predominantly based on ionic interactions. Therefore, a solid support bearing positively charged groups is preferably used, in particular a solid support bearing groups that can be positively charged by protonation. A variety of such solid supports is commercially available or can be prepared by common techniques. In one embodiment the solid support is functionalized with positively charged groups, preferably groups that are positively charged by protonation, and the negatively charged polyanion $[M'M_{12}X_8O_yR_zH_q]$ is linked to said positively charged groups by electrostatic interactions. In a preferred embodiment the solid support, preferably mesoporous silica, more preferably SBA-15 or MCM-41, most preferably SBA-15, is functionalized with moieties bearing positively charged groups, preferably tetrahydrocarbyl ammonium groups, more preferably groups that can be positively charged by protonation, most preferably monofunctionalized amino groups —$NH_2$. Preferably said groups are attached to the surface of the solid support by covalent bonds, preferably via a linker that comprises one or more, preferably one, of said groups, preferably an alkyl, aryl, alkenyl, alkynyl, hetero-alkyl, hetero-cycloalkyl, hetero-alkenyl, hetero-cycloalkenyl, hetero-alkynyl, hetero-aryl or cycloalkyl linker, more preferably an alkyl, aryl, hetero-alkyl or hetero-aryl linker, more preferably an alkyl linker, most preferably a methyl, ethyl, n-propyl, n-butyl, n-pentyl, n-hexyl linker, in particular a n-propyl linker. Preferably said linkers are bonded to any suitable functional group present on the surface of the solid support, such as to hydroxyl groups. Preferably said linkers are bonded to said functional groups present on the surface of the solid support either directly or via another group or atom, most preferably via another group or atom, preferably a silicon-based group, most preferably a silicon atom. In a most preferred embodiment of the present invention the POMs are supported on (3-aminopropyl)triethoxysilane (apts)-modified SBA-15.

In the supported POMs of the present invention, the POMs that are immobilized on the solid support are in the form of primary and/or secondary particles. In an especially preferred embodiment, the immobilized POMs particles are mainly in the form of primary particles (i.e. non-agglomerated primary particles), that is at least 90 wt % of the immobilized POMs particles are in the form of primary particles, preferably at least 95 wt %, more preferably at least 99 wt %, in particular substantially all the immobilized POMs particles are in the form of primary particles.

The invention is further directed to processes for preparing supported POMs according to the invention. Solid supports used in the context of this invention are as defined above. In a preferred embodiment of the present invention the surface of the solid supports is modified with positively charged groups, more preferably groups that can be positively charged by protonation. Those charged solid supports can be prepared by techniques well established in the art, for example by the surface modification of a mesoporous silica, such as SBA-15, with a suitable reagent bearing a positively charged group or a group that can be positively charged by protonation, such as 3-aminopropyltriethoxysilane (apts), is conducted by heating, preferably under reflux, under inert gas atmosphere, such as argon or nitrogen, in an inert solvent with a suitable boiling point, such as hexane, heptane or toluene, for a suitable time, such as 4-8 hours, and finally the modified solid support is isolated, preferably by filtration, purified, preferably by washing, and dried, preferably under vacuum by heating, most preferably under vacuum by heating at about 100° C.

The optionally treated support may be further calcined at a temperature of 500° C. to 800° C. For the calcination, common equipment may be used, that is commercially available. Calcination of the optionally treated support may for instance be conducted under an oxygen containing gas such as air, under vacuum, under hydrogen or under an inert gas such as argon or nitrogen, more preferably under inert gas, most preferably under nitrogen.

The POMs according to the present invention or prepared by the process of the present invention can be immobilized on the surface of the solid support by contacting said POMs with the solid support. The present invention therefore also relates to a process for the preparation of supported POMs, comprising the step of contacting the POMs provided by the present invention or prepared according to the present invention with the solid support, thereby immobilizing at least part of the POMs onto the support; and optionally isolating the resulting supported POMs.

Said contacting may be conducted employing common techniques in the art, such as blending both the solid support and the POM in the solid form. In a preferred embodiment the POM is mixed with a suitable solvent, preferably water or an aqueous solvent, and the solid support is added to this mixture. In a more preferred embodiment the solid support is mixed with a suitable solvent, preferably water or an aqueous solvent, and the POM is added to this mixture. In case a solid support with groups that can be positively charged by protonation is used, the mixture is preferably acidified, for instance by addition of $H_2SO_4$, $HNO_3$ or HCl, most preferably by addition of $H_2SO_4$ or $HNO_3$, so that the pH value of the mixture ranges from 0.1 to 6, preferably from 1 to 4 and more preferably from 1.5 to 3, most preferably is a pH of about 2. The mixture comprising POM, solid support and solvent is preferably stirred, typically for 1 min to 24 h, more preferably for 30 min to 15 h, more preferably for 1 h to 12 h, most preferably for 6 h to 10 h, in particular about 8 h. While stirring, preferably the mixture is heated to a temperature of from 20° C. to 100° C., preferably from 20° C. to 80° C., preferably from 20° C. to 60° C., preferably from 20° C. to 40° C., and most preferably about 25° C. Afterwards, the supported POM can be kept in the solvent as suspension or can be isolated. Isolation of the supported POM from the solvent may be performed by any suitable method in the art, such as by filtration, evaporation of the solvent, centrifugation or decantation, preferably by filtration or removal of the solvent in vacuum, more preferably by filtration. The isolated supported POMs may then be washed with a suitable solvent, preferably water or an aqueous solvent, and dried. Supported POMs may be dried in an oven at a temperature of e.g. about 100° C.

In another embodiment, the supported POMs may be further calcined at a temperature not exceeding the transformation temperature of the POM, i.e. the temperature at which decomposition of the POM starts to take place (usually about 600-700° C. for the present POMs according to their corresponding TGA). Thus, in a preferred embodiment the POMs of the present invention are thermally stable up to temperatures of around 600-700° C. For the calcination, common equipment may be used, that is commercially available. Calcination of the supported POMs may for instance be conducted under an oxygen containing gas such as air, under vacuum, under hydrogen or under an inert gas such as argon or nitrogen, more preferably under inert gas, most preferably under nitrogen.

In many cases, however, and in particular if the supported POM is used as a catalyst or pre-catalyst under reductive conditions, drying of the supported POM without calcination may be sufficient.

In supported POMs, the POM loading levels on the solid support may be up to 30 wt % or even more but are preferably up to 10 wt %, for instance up to 5 wt % or even up to 2 wt %. Accordingly, the POM loading level on the solid support is typically of 0.01 to 30 wt %, particularly 0.05 to 20 wt %, more particularly 0.1 to 10 wt %, often 0.2-6 wt %, more often 0.3-5 wt %, and most often 0.5-2 wt %. POM loading levels on the solid support can be determined by elemental analysis such as Inductively Coupled Plasma Mass Spectrometry (ICP-MS) analysis, for instance using a Varian Vista MPX.

According to one embodiment, the present invention also relates to a metal cluster of the formula

wherein
each $M^o$ is independently selected from the group consisting of $Pd^o$, $Pt^o$, $Rh^o$, $Ir^o$, $Ag^o$, and $Au^o$, preferably $Pd^o$, $Pt^o$, $Rh^o$, $Ir^o$, and $Au^o$, more preferably $Pd^o$, $Pt^o$ and $Rh^o$, most preferably $Pd^o$ and $Pt^o$, in particular $Pd^o$, and M' is selected from the group consisting of Ga, In, Tl, Ge, Sn, Pb, Sb, and Bi and the oxidation state of M' is 0 or greater than 0, preferably 0 to V, more preferably 0, III, IV or V, most preferably 0 or IV, in particular 0.

In a preferred embodiment, M' in the metal cluster $[M'M^o_{12}]$ is selected from the group consisting of Ge, Sn, Pb, Sb, and Bi, most preferably Ge, Sn and Pb, in particular Sn.

In a preferred embodiment, all $M^o$ in the metal cluster $[M'M^o_{12}]$ are the same, in particular all $M^o$ are $Pd^o$ or $Pt^o$, especially $Pd^o$. The metal cluster $[M''M^o_{12}]$ comprises at least two different types of metal atoms ($M^o \neq M'$). Since the $M^o$ are independently selected and hence may be different among each other, the metal cluster [M'M$^o_{12}$] may comprise more than two different types of metal atoms. In an embodiment of the present invention, the M$^o$ are different among each other in the metal cluster [M'M$^o_{12}$] and hence, in said embodiment, the metal cluster [M'M$^o_{12}$] comprises 3 to 7 different types of metal atoms, preferably 3, 4 or 5, more preferably 3, 4, most preferably 3. However, in an especially preferred embodiment, all M$^o$ in the metal cluster [M'M$^o_{12}$] are the same and hence, in said embodiment, the metal cluster [M'M$^o_{12}$] comprises two different types of metal atoms.

In this context, M$^o$≠M' either means that all M$^o$ are the same among each other, and hence all M$^o$ are different from M'; or that the M$^o$ are different among each other, but still all M$^o$ are different from M'.

The above considerations apply mutatis mutandis also to the formula $(A_n)^{m+}[M'M_{12}X_8O_yR_zH_q]^{m-}$ of the POM.

In an especially preferred embodiment, the invention relates to metal clusters represented by the formula [SnPd$_{12}$], in particular [SnPd$^o_{12}$].

Further, suitable examples of metal clusters according to the invention are represented by the formulae

[M'M$^o_{12}$], e.g.,

[M'Pd$^o_{12}$], such as

[GaPd$^o_{12}$],

[GePd$^o_{12}$],

[InPd$^o_{12}$],

[TlPd$^o_{12}$],

[PbPd$^o_{12}$],

[SbPd$^o_{12}$], or

[BiPd$^o_{12}$],

[M'Pt$^o_{12}$],

[SnM$^o_{12}$], such as

[SnPt$^o_{12}$],

[SnRh$^o_{12}$],

[SnIr$^o_{12}$]

[SnAg$^o_{12}$], and

[SnAu$^o_{12}$].

The metal clusters of the present invention are in the form of primary and/or secondary particles. In an especially preferred embodiment, the metal clusters provided by the present invention are mainly in the form of primary particles (i.e. non-agglomerated primary particles), that is at least 90 wt % of the metal clusters are in the form of primary particles, preferably at least 95 wt %, more preferably at least 99 wt %, in particular substantially all the metal clusters are in the form of primary particles. This includes metal clusters dispersed in liquid carrier media. The metal clusters of the present invention preferably have a primary particle size of about 1.0-2.0 nm, for instance about 1.5 nm.

In a further embodiment, the metal clusters are dispersed in a liquid carrier medium, thereby forming a dispersion of metal clusters. In one embodiment of the present invention the liquid carrier medium is an organic solvent, optionally combined with one or more dispersing agents. The organic solvent is preferably capable of dissolving the POMs used as starting material for the preparation of the metal clusters, for instance liquid n-alkanes, e.g., hexane or heptane.

The dispersing agent (or surfactant) is added to the liquid carrier medium to prevent agglomeration of the primary particles of metal cluster. Preferably, the dispersing agent is present during formation of the primary particles of metal cluster. An example of a surfactant useful as dispersing agent is citric acid or citrate. The dispersing agent preferably forms micelles, each micelle containing one primary particle of metal cluster thereby separating the primary particles from each other and preventing agglomeration thereof.

In another further embodiment, the metal clusters can be immobilized on a solid support thereby forming supported metal clusters. Suitable supports include but are not limited to materials having a high surface area and/or a pore size which is sufficient to allow the metal clusters to be loaded, e.g. polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous materials, like mesoporous silica, such as SBA-15 and MCM-41, zeolites, aluminophosphates (ALPO s), silicoaluminophosphates (SAPOs), metal organic frameworks (MOFs), zeolitic imidazolate frameworks (ZIFs), periodic mesoporous organosilicas (PMOs), and mixtures thereof and modified compounds thereof. Preferred supports are, for instance, mesoporous silica, more preferably SBA-15 or MCM-41, most preferably SBA-15.

A variety of such solid supports is commercially available or can be prepared by common techniques. Furthermore, there are various common techniques to modify or functionalize solid supports, for example with regard to the size and shape of the surface or the atoms or groups available for bonding on the surface. In a preferred embodiment of the present invention the immobilization of the metal clusters to the surface of the solid support is accomplished by means of adsorption, including physisorption and chemisorption, preferably physisorption. The adsorption is based on interactions between the metal clusters and the surface of the solid support, such as van-der-Waals interactions.

In the supported metal clusters of the present invention, the metal clusters that are immobilized on the solid support are in the form of primary and/or secondary particles. In an especially preferred embodiment, the immobilized metal cluster particles are mainly in the form of primary particles (i.e. non-agglomerated primary particles), that is at least 90 wt % of the immobilized metal cluster particles are in the form of primary particles, preferably at least 95 wt %, more preferably at least 99 wt %, in particular substantially all the immobilized metal cluster particles are in the form of primary particles.

In the supported metal clusters of the present invention, the metal cluster loading levels on the solid support may be up to 30 wt % or even more but are preferably up to 10 wt %, for instance up to 5 wt % or even up to 2 wt %. Accordingly, the metal cluster loading level on the solid support is typically of 0.01 to 30 wt %, particularly 0.05 to 20 wt %, more particularly 0.1 to 10 wt %, often 0.2-6 wt %, more often 0.3-5 wt %, and most often 0.5-2 wt %. Metal cluster loading levels on the solid support can be determined by elemental analysis such as Inductively Coupled Plasma Mass Spectrometry (ICP-MS) analysis, for instance using a Varian Vista MPX.

The invention is further directed to processes for preparing metal clusters according to the invention.

Among the preferred processes for preparing any one of the metal clusters of the present invention is a process for the preparation of a dispersion of said metal clusters dispersed in liquid carrier media. Said process comprises:
- (a) dissolving any one of the POMs provided by the present invention or prepared according to the present invention in a liquid carrier medium,
- (b) optionally providing additive means to prevent agglomeration of the metal clusters to be prepared, preferably adding compounds capable of preventing agglomeration of metal clusters to be prepared, more preferably adding surfactants to enable micelle formation, and
- (c) subjecting the dissolved POM to chemical or electrochemical reducing conditions sufficient to at least partially reduce said POM into corresponding metal clusters.

In a preferred embodiment in step (a), the liquid carrier medium capable of dissolving the POM used for the preparation of the metal clusters is an organic solvent, such as liquid n-alkanes, e.g., hexane or heptane.

In a preferred embodiment in step (b), classical capping groups such as diverse types of inorganic and organic anions, such as carboxylates, e.g. citrate, may be used to prevent agglomeration of the metal clusters to be prepared.

In a preferred embodiment in step (c), the chemical reducing conditions comprise the use of a reducing agent selected from organic and inorganic materials which are oxidizable by $Pd^{II}$, $Pt^{II}$, $Rh^{I}$, $Ir^{I}$, $Ag^{I}$ and $Ag^{III}$, and $Au^{I}$ and $Au^{III}$. Such a chemical reduction can for example be effected by using borohydrides, aluminohydrides, hydrazine, CO or hydrogen, preferably hydrogen, more preferably hydrogen at elevated temperature and pressure, preferably by using hydrogen. In the alternative, the POM in step (c) is reduced electrochemically using a common electrochemical cell.

The metal clusters of the present invention can be immobilized on the surface of a solid support. The present invention therefore also relates to processes for the preparation of supported metal clusters according to the present invention. A first process for the preparation of supported metal clusters comprises contacting the dispersion of metal clusters provided by the present invention or prepared according to the present invention with a solid support, thereby immobilizing at least part of the dispersed metal clusters onto the support; and optionally isolating the supported metal clusters.

In a preferred embodiment, the solid support is added to the dispersion of metal clusters. The resulting mixture is preferably stirred, typically for 1 min to 24 h, more preferably for 30 min to 15 h, more preferably for 1 h to 12 h, most preferably for 6 h to 10 h, in particular about 8 h. While stirring, preferably the mixture is heated to a temperature of from 20° C. to 100° C., preferably from 20° C. to 80° C., preferably from 20° C. to 60° C. preferably from 20° C. to 40° C., and most preferably about 25° C. Afterwards, the supported metal clusters are preferably isolated. Isolation of the supported metal clusters from the solvent may be performed by any suitable method in the art, such as by filtration, evaporation of the solvent, centrifugation or decantation, preferably by filtration or removal of the solvent in vacuum, more preferably by filtration. The isolated supported metal clusters may then be washed with a suitable solvent, preferably water or an aqueous solvent, and dried, for instance by heating under vacuum.

Another suitable process for the preparation of supported metal clusters according to the present invention comprises: subjecting supported POM provided by the present invention or prepared according to the present invention to chemical or electrochemical reducing conditions sufficient to at least partially reduce said POM into corresponding metal clusters; and optionally isolating the supported metal clusters.

In a preferred embodiment, the chemical reducing conditions comprise the use of a reducing agent selected from organic and inorganic materials which are oxidizable by $Pd^{II}$, $Pt^{II}$, $Rh^{I}$, $Ir^{I}$, $Ag^{I}$ and $Ag^{III}$, and $Au^{I}$ and $Au^{III}$. Such a chemical reduction can for example be effected by using borohydrides, aluminohydrides, hydrazine, CO or hydrogen, preferably hydrogen, more preferably hydrogen at elevated temperature and pressure. In the alternative, the POM is reduced electrochemically using a common electrochemical cell.

The invention is also directed to the use of optionally supported POMs provided by the present invention or prepared according to the present invention and/or optionally supported or dispersed metal clusters provided by the present invention or prepared according to the present invention, for catalyzing homogeneous and heterogeneous reductive conversion of organic substrates.

In a preferred embodiment, reductive conversion refers to homogeneous or heterogeneous reduction and/or hydroprocessing and/or hydrocracking and/or (hydro)desulfurization of organic substrate.

Within the present reductive conversion of organic substrates, a variety of reducing reagents can be used, including hydrogen or a hydrogen-containing atmosphere.

Since the M metal atoms are not fully sterically shielded by the polyanion backbone, various noble metal coordination sites are easily accessible to the organic substrate and the reducing reagent or reduction active transfer molecule and therefore high catalytic activities are achieved. Further, the remarkable thermal stability of the optionally supported POMs of the present invention permits their use under a great variety of reaction conditions.

Compared with the optionally supported POMs of the present invention, the accessibility of the noble metal atoms in the optionally supported or dispersed metal clusters of the present invention is even better because of the absence of any ligands. Further, the remarkable thermal stability of the optionally supported or dispersed metal clusters of the present invention is at least comparable to the one of the optionally supported POMs therefore permitting their use under a great variety of reaction conditions.

It is contemplated that the optionally supported POMs of the present invention can be reduced under the reductive reaction conditions of the reductive conversion described herein. Thus, it might be possible that the optionally supported POMs are reductively converted into metal cluster-like structures or even into metal clusters under the conversion reaction conditions and it might be possible that said metal cluster-like structures or said metal clusters are actually the catalytically active species. Nevertheless, the optionally supported POMs of the present invention give excellent results in homogeneous and heterogeneous reductive conversion of organic substrates, regardless of the specific nature of the actually catalytically active species.

Another useful aspect of this invention is that the optionally supported POMs and/or optionally supported or dispersed metal clusters of the present invention can be recycled and used multiple times for the reduction of organic molecules.

In a preferred embodiment this invention thus also relates to a process for reducing organic substrates comprising the steps:

(a) contacting a first organic substrate under addition of hydrogen with one or more optionally supported POMs and/or one or more supported metal clusters,
(b) recovering the one or more optionally supported POMs and/or one or more supported metal clusters;
(c) contacting the one or more optionally supported POMs and/or one or more supported metal clusters with a solvent at a temperature of 50° C. or more, and/or hydrogen stripping the one or more optionally supported POMs and/or the one or more supported metal clusters at elevated temperature, and/or calcining the one or more optionally supported POMs and/or the one or more supported metal clusters at elevated temperature under an oxygen containing gas, e.g. air, or under an inert gas, e.g. nitrogen or argon, to obtain a recycled one or more optionally supported POMs and/or one or more supported metal clusters;
(d) contacting the recycled one or more optionally supported POMs and/or one or more supported metal clusters under addition of hydrogen with a second organic substrate which may be the same as or different from the first organic substrate; and
(e) optionally repeating steps (b) to (d).

The contacting of organic substrate under addition of hydrogen with optionally supported POM and/or supported metal cluster in step (a) may e.g. be carried out in a continuously stirred tank reactor (CSTR), a fixed bed reactor, a fluidized bed reactor or a moving bed reactor.

Thus, e.g., the optionally supported POMs and/or supported metal clusters of the present invention can be collected after a reduction reaction, washed with a polar or non-polar solvent such as acetone and then dried under heat (typically 50° C. or more, alternately 100° C. or more, alternately 125° C. or more, alternately 150° C. or more) for 30 minutes to 48 hours, typically for 1 to 24 hours, more typically for 2 to 10 hours, more typically for 3 to 5 hours.

Alternatively to or in addition to the washing, the optionally supported POMs and/or supported metal clusters may be subjected to hydrogen stripping at elevated temperature. Preferably, the hydrogen stripping is carried out at a temperature of 50° C. or higher, more preferably in the range from 200° C. to 500° C. and most preferably from 350° C. to 500° C.

Alternatively to or in addition to the washing and/or hydrogen stripping, the optionally supported POMs and/or supported metal clusters may be calcined at elevated temperature under an oxygen containing gas, e.g. air, or under an inert gas, e.g. nitrogen or argon. Preferably, the calcination is carried out at a temperature in the range from 600° C. to 700° C. The calcination can also be carried out at a lower temperature such as at a temperature from 250° C. to 600° C., such as from 300° C. to 600° C. or from 300° C. to 500° C.

The washing and/or hydrogen stripping and/or calcining has the effect of regenerating the optionally supported POMs and/or supported metal clusters for recycling.

The recycled optionally supported POMs and/or supported metal clusters of the present invention may be used on fresh organic molecules, or on recycled organic molecules from a recycle stream.

It is preferred to use supported POMs and/or supported metal clusters of the present invention as catalysts with regard to recovery and recycling of the catalyst in the reductive conversion processes described herein. Advantageously, the supported POMs and/or supported metal clusters of the present invention may be recycled and used again under the same or different reaction conditions. Typically the supported POMs and/or supported metal clusters are recycled at least 1 time, preferably at least 4 times, preferably at least 8 times, preferably at least 12 times, preferably at least 100 times.

Thus, this invention also relates to a process for reducing organic substrates (typically an arene) which process comprises contacting a first organic substrate with one or more supported POMs and/or supported metal clusters of the present invention, thereafter recovering the supported POMs and/or supported metal clusters of the present invention, contacting the supported POMs and/or supported metal clusters of the present invention with a solvent (such as acetone) at a temperature of 50° C. or more, and/or hydrogen stripping the supported POMs and/or supported metal clusters at elevated temperature, and/or calcining the supported POMs and/or supported metal clusters to obtain recycled supported POMs and/or supported metal clusters of the present invention, thereafter contacting the recycled supported POMs and/or supported metal clusters of the present invention with a second organic substrate, which may be the same as or different from the first organic substrate, this process may be repeated many times, preferably at least 4 times, preferably at least 8 times, preferably at least 12 times, preferably at least 100 times.

Due to the definite stoichiometry of POMs, the optionally supported POMs of the present invention can be converted (e.g. by calcination at a temperature exceeding the transformation temperature) to mixed metal-oxide catalysts in a highly reproducible manner Consequently, the optionally supported POMs according to the present invention can also be used as a precursor for mixed metal-oxide catalysts.

Metal clusters of the present invention, optionally supported or dispersed in a liquid carrier medium, can be described as nanocatalysts of M' and M at the atomic or molecular level, i.e., particles of M' and M having an average diameter of about 1.0-2.0 nm, for instance about 1.5 nm, obtained by reduction of the POMs. In the case of the preferred embodiment, wherein all M are the same, nanocatalysts with exactly one noble atom species and with exactly one post-transition metal species are obtained. In another embodiment in which at least one or more M are different among each other nanocatalysts with exactly one post-transition metal species and with 2 to 6 noble atom species, preferably 2, 3 or 4, more preferably 2 or 3, most preferably 2, are obtained. Thus, the bottom-up approach of the present invention allows for the preparation of noble metal-rich customized nanocatalysts of very well defined size and shape, in which two or more than two metal species can be selected individually from groups that contain or consist of the noble metal elements Rh, Ir, Pd, Pt, Ag, and Au and post-transition metal elements Ga, In, Tl, Ge, Sn, Pb, Sb, and Bi.

The obtained metal clusters can be used for a wide range of catalytic applications such as in fuel cells, for detection of organic substrates, selective hydrogenation, reforming, hydrocracking, hydrogenolysis and oligomerization. Besides immobilizing the present POMs on a matrix surface and subsequently reducing them, the deposition of the POMs on a surface matrix and their reduction can also be carried out simultaneously.

In addition, e.g., the POMs according to the invention such as a $[SnPd_{12}P_8O_{40}]^{12-}$ polyanion can be used to produce modified electrodes by electrochemical deposition of the POM on an electrode surface such as a glassy carbon (GC) electrode surface. The obtained deposits contain predominantly $M^0$ such as $Rh^0$, $Ir^0$, $Pd^0$, $Pt^0$, $Ag^0$, $Au^0$, and preferably mixtures thereof with very small amounts $M^{y+}$ such as $Pd^{II}$, $Pt^{II}$, $Rh^{I}$, $Ir^{I}$, $Ag^{I}$, $Ag^{III}$, $Au^{I}$, and $Au^{III}$ and mixtures thereof, preferably $Pd^{II}$, $Pt^{II}$, $Rh^{I}$, $Rh^{I}$, $Ir^{I}$, $Ag^{I}$, and $Ag^{III}$. In a preferred embodiment, the obtained deposits provide improved electrochemical behaviors like improved kinetics of electrocatalytic processes compared to a film deposited using a conventional precursor of M and M'. For example, electrodes modified with a deposit of the present POMs can be used for the electrochemical reduction of organic substrates. It has been found that such modified electrodes show a very small overpotential and a remarkably high shelf life.

EXAMPLES

The invention is further illustrated by the following examples.

Example 1: Synthesis of $Na_{12}[SnPd_{12}P_8O_{40}]\cdot 43H_2O$ $Pd(CH_3COO)_2$ (0.023 g, 0.100 mmol) and $SnCl_4 \cdot 5H_2O$ (0.009 g, 0.025 mmol) were dissolved in 0.5 M $NaH_2PO_4$ solution (2 mL, 1 mmol, pH 6.9). The solution was heated to 80° C. under stirring and during the first 30 minutes the pH of the solution was adjusted to about 8.0 by addition of 1 M NaOH. The resulting solution was heated at 80° C. for another 60 minutes. Then the solution was allowed to cool to room temperature, filtered, and the filtrate left for crystallization at room temperature in an open vial. Dark red, block-shaped crystals were obtained after 2 weeks, which were collected by filtration and air-dried. Yield: 0.011 g (38% based on Pd). This product was analyzed by XRD, IR, elemental analysis, TGA and $^{31}P$ NMR and was identified as $[SnPd_{12}P_8O_{40}]^{12-}$ polyanion ("$SnPd_{12}$"), isolated as hydrated sodium salt $Na_{12}[SnPd_{12}P_8O_{40}]43H_2O$ ("Na—$SnPd_{12}$")

Example 2: Analysis of "Na—$SnPd_{12}$"

The IR spectrum with 4 $cm^{-1}$ resolution was recorded on a Nicolet Avatar 370 FT-IR spectrophotometer on KBr pellet sample (peak intensities: w=weak; m=medium; s=strong). The characteristic region of the polyanion is between 1000-400 $cm^{-1}$ due to metal-oxygen stretching vibrations: 1635 (m), 1417 (w), 1263 (w), 1130 (s), 1070 (m), 954 (s), 920 (w), 867 (w), 821 (w), 623 (s), 540 (w), 517 (w). The FT-IR spectrum is shown in FIG. 4. Absorption bands that correspond to different vibrational modes of Pd—O groups appear in the regions between 623 and 517 $cm^{-1}$. Absorption bands between 1130 and 920 $cm^{-1}$ are attributed to the phosphate heterogroups. The absorption band near 1635 $cm^{-1}$ belongs to asymmetric vibrations of the crystal waters.

Elemental analysis for "Na—$SnPd_{12}$" calculated (found): Na 8.27 (8.74), Sn 3.56 (3.28), Pd 38.30 (37.72), P 7.43 (7.40).

Thermogravimetric analysis (TGA) was performed on a SDT Q 600 device from TA Instruments with 10-30 mg samples in 100 µL alumina pans, under a 100 mL/min $N_2$ flow with a heating rate of 5° C./min between 20° C. and 800° C. (FIG. 1). Only one weight-loss step was observed on the thermogram below 620° C. This result is in good agreement with that obtained by elemental analysis to determine the amount of water of crystallization present in the POM.

Example 3: Single Crystal X-ray Diffraction (XRD) Data and Aanalysis of "Na—$SnPd_{12}$"

Besides IR, elemental analysis and TGA the product was also characterized by single-crystal XRD. The crystal was mounted in Hampton cryoloop at 100 K using light oil for data collection. Indexing and data collection were carried on a Bruker Kappa X8 APEX II CCD single crystal diffractometer with κ geometry and Mo Kα radiation (λ=0.71073 Å). The SHELX software package (Bruker) was used to solve and refine the structure. An empirical absorption correction was applied using the SADABS program as disclosed in G. M. Sheldrick, SADABS, Program for empirical X-ray absorption correction, Bruker-Nonius: Madison, Wis. (1990). The structure was solved by direct method and refined by the full-matrix least squares method ($\Sigma w(|F_o|^2 - |F_c|^2)^2$) with anisotropic thermal parameters for all heavy atoms included in the model. The H atoms of the crystal waters were not located. Also, it was not possible to locate all sodium counter cations by XRD, due to crystallographic disorder. The exact number of counter cations and crystal water in the POM were thus based on elemental analysis. Compound "Na—$SnPd_{12}$" crystallizes in the cubic space group Fm-3m. Crystallographic data are detailed in Table 1.

TABLE 1

| Crystal data for "Na—$SnPd_{12}$" | |
|---|---|
| Empirical formula | $Na_{12}SnPd_{12}P_8H_{86}O_{83}$ |
| Formula weight, g/mol | 3334.05 |
| Crystal system | Cubic |
| Space group | Fm-3m |
| a, Å | 20.0624(2) |
| b, Å | 20.0624(2) |
| c, Å | 20.0624(2) |
| α, ° | 90.00 |
| β, ° | 90.00 |
| γ, ° | 90.00 |
| Volume, Å$^3$ | 8075.1(2) |
| Z | 4 |
| $D_{calc}$, g/cm$^3$ | 2.742 |
| Absorption coefficient, mm$^{-1}$ | 3.262 |
| F(000) | 6416 |
| Theta range for data collection, ° | 1.76 to 45.76 |
| Completeness to $\Theta_{max}$ % | 99.8 |
| Index ranges | −18 <= h <= 40, |
| | −39 <= k <= 40, |
| | −40 <= l <= 39 |
| Reflections collected | 103139 |
| Independent reflections | 1770 |
| R(int) | 0.0532 |
| Absorption correction | Semi-empirical from equivalents |
| Data/restraints/parameters | 1770/13/32 |
| Goodness-of-fit on F$^2$ | 1.056 |
| $R_1^{[a]}$, $wR_2^{[b]}$ (I > 2σ(I)) | $R_1$ = 0.0338, $wR_2$ = 0.1270 |
| $R_1^{[a]}$, $wR_2^{[b]}$ (all data) | $R_1$ = 0.0480, $wR_2$ = 0.1625 |
| Largest diff. peak and hole, e/Å$^3$ | 2.227 and −3.784 |

[a]$R_1 = \Sigma ||F_o| - |F_c||/\Sigma |F_o|$,
[b]$wR_2 = [\Sigma w (F_o^2 - F_c^2)^2/\Sigma w(F_o^2)^2]^{1/2}$

Example 4: Structure of "$SnPd_{12}$" Polyanion

The structure of "$SnPd_{12}$" polyanion is displayed in FIGS. 2 and 3. The central $Sn^{IV}$ ion has a cubic geometry and is coordinated by eight oxygen atoms leading to a {$SnO_8$} cuboid fragment (SnO of 2.223(5) Å) in which each µ$_4$-oxo ligand bridges the central $Sn^{IV}$ and three $Pd^{II}$ ions. The twelve $Pd^{II}$ ions all adopt a square-planar geometry and form a distorted cuboctahedron around the central guest atom $Sn^{IV}$. The resulting {$SnO_8Pd_{12}O_{24}$} assembly has 24 additional "outer" oxygens forming a truncated cubic shell which is in turn capped by eight $OP^{3+}$ groups. The eight $OP^{3+}$ groups cap the eight triangular faces of the {$SnO_8Pd_{12}O_{24}$} cuboctahedron assembly to form a distorted cube. In the alternative, "$SnPd_{12}$" polyanion can thus also be described as $[SnO_8Pd_{12}O_{24}(PO)_8]^{12-}$.

Example 5: $^{31}$P NMR Spectrum of "Na—SnPd$_{12}$"

"Na—SnPd$_{12}$" crystals were dissolved in H$_2$O/D$_2$O. $^{31}$P NMR spectrum was recorded at room temperature on a 400 MHz JEOL ECX instrument, using 5 mm tube with resonance frequency 162.14 MHz. The chemical shift is reported with respect to the reference 85 wt % H$_3$PO$_4$. The $^{31}$P NMR spectrum is shown in FIG. 5.

Example 6: Synthesis of Supported "SnPd$_{12}$"

Synthesis of Mesoporous Silica Support SBA-15

8.0 g of Pluronic® P-123 gel (Sigma-Aldrich) were added to 40 mL of 2 M HCl and 208 mL H$_2$O. This mixture was stirred for 2 hours in a water bath at 35° C. until it was completely dissolved. Then 18 mL of tetraethylorthosilicate (TEOS) was added dropwise, and the mixture was kept under stirring for 4 hours. Afterwards, the mixture was heated in an oven at 95° C. for 3 days. The white precipitate was collected by filtration, washed and air-dried. Finally, the product was calcined by heating the as-synthesized material to 550° C. at a rate of 1-2° C./min and kept at 550° C. for 6 hours to remove the templates.

Synthesis of Modified SBA-15-apts 1.61 mL of 3-aminopropyltriethoxysilane (apts) was added to 3 g of SBA-15, prepared according to the synthesis described above, in 90 mL toluene. This mixture was refluxed for 5 hours and then filtered at room temperature. The obtained modified SBA-15-apts was heated at 100° C. for 5 hours.

Preparation of "SnPd$_{12}$" supported on SBA-15-apts (supported "SnPd$_{12}$")

"Na—SnPd$_{12}$" was dissolved in water (0.056 mmol/L), resulting in a colored solution. While stirring, SBA-15-apts was slowly added to the solution of "Na—SnPd$_{12}$" so that the respective amounts of "Na—SnPd$_{12}$" and SBA-15-apts were 5 wt % and 95 wt %, respectively. The mixture was kept under stirring for 24 hours at 40° C., filtered and then washed three times with water. The filtrate was colorless, indicating that the "Na—SnPd$_{12}$" POM was quantitatively loaded on the SBA-15-apts support, leading to a "Na—SnPd$_{12}$" POM loading level on the solid support of about 5 wt %. The supported product was then collected and air-dried.

Example 7: Activation of Supported "Na—SnPd$_{12}$" and Preparation of Supported "SnPd$_{12}$" Metal Clusters The supported "Na—SnPd$_{12}$" prepared according to example 6 was activated or transformed into the corresponding supported metal clusters before testing its catalytic hydrogenation properties.

In a first example 7a, supported "Na—SnPd$_{12}$" prepared according to example 6 was activated by air calcination at 300° C. for 3 hours. In a second example 7b, supported "Na—SnPd$_{12}$" prepared according to example 6 was converted into corresponding supported "SnPd$_{12}$" metal clusters by H$_2$ reduction at 300° C., 50 bar for 24 hours. In a third example 7c, supported "Na—SnPd$_{12}$" prepared according to example 6 was treated by the same method of example 7b, but followed with air calcination at 550° C. for 4.5 hours. In a fourth example 7d, supported "Na—SnPd$_{12}$" prepared according to example 6 was converted into corresponding supported "SnPd$_{12}$" metal clusters by a chemical reduction conducted by suspending 100 mg of supported "Na—SnPd$_{12}$" in 15 mL of water followed by the addition of about 0.25 mL of hydrazine hydrate. The resulting solution was stirred for 12 hours, filtered, dried and then air calcined at 300° C. for 3 hours. Without being bound by any theory, it is believed that calcination and optional hydrogenation or chemical reduction helps to activate the POM by forming active sites.

Example 8: Catalytic Activity of Supported "Na—SnPd$_{12}$" and Supported "SnPd$_{12}$" Metal Clusters The activated supported "Na—SnPd$_{12}$" POM of example 7a and the supported "SnPd$_{12}$" metal clusters of examples 7b, 7c and 7 d were tested for catalytic hydrogenation of o-xylene.

The hydrogenation of o-xylene was carried out in a 100 mL Parr 5513 stainless steel high-pressure Compact Reactor equipped with a magnetically coupled stirrer drive ensuring a well-mixed environment of reactants. The reaction mixture contained 3.5 mL of o-xylene in 47.5 mL hexane and 50 mg of activated supported "Na—SnPd$_{12}$" POM or supported "SnPd$_{12}$" metal clusters (5 wt %) and was stirred at 1500 rpm. The autoclave was purged with H$_2$ and then heated and pressurized to the desired set point of temperature (300° C.) and pressure (90 bar) respectively. In order to prove catalyst recyclability, adding a new portion of substrate into the reactor after reaction completion followed all catalytic runs (i.e., running more than one cycle).

The reaction was followed by H$_2$ consumption and gas chromatography (GC) analysis. A GC-2010 Shimadzu instrument equipped with a flame ionization detector (FID) was used to measure substrate conversion and selectivity of obtained products via a HP-5 column (15 m×0.25 mm) providing good separation of reaction products. The carrier gas was He. This overall procedure ensured good reproducibility of the catalytic experiments.

The SBA-15-apts support alone did not show any hydrogenation activity while activated supported "Na—SnPd$_{12}$" POM and supported "SnPd$_{12}$" metal clusters showed catalytic performances with full conversion of o-xylene to cis/trans-1,2-dimethylcyclohexane. The conversion and cis/trans selectivity (expressed as cis/trans molar ratio) obtained for the activated supported "Na—SnPd$_{12}$" POM and supported "SnPd$_{12}$" metal clusters are summarized in Table 4 below.

TABLE 4

| | Catalytic performance | | |
|---|---|---|---|
| Sample | Time (min) | Conversion (mol %) | Cis/trans selectivity |
| 7a | 31 | ≈100 | 40/60 |
| 7b | 70 | ≈100 | 40/60 |
| 7c | 42 | ≈100 | 43/57 |
| 7d | 200 | ≈100 | 40/60 |

The catalytic performance of the activated supported "Na—SnPd$_{12}$" POM and supported "SnPd$_{12}$" metal clusters was thus excellent compared to other commercial catalysts.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

Additionally or alternately, the invention relates to:

Embodiment 1: A polyoxometalate represented by the formula

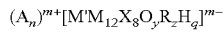

or solvates thereof, wherein
each A independently represents a cation,
n is the number of cations,
each M is independently selected from the group consisting of Pd, Pt, Rh, Ir, Ag and Au, and each M has $d^8$ valence electron configuration,
M' is selected from the group consisting of Ga, In, Tl, Ge, Sn, Pb, Sb, and Bi, each X is independently selected from the group consisting of Al, Si, P, As, S, Se, Te and mixtures thereof,
each R is a substituent group which is covalently bonded to X, and each R is independently selected from the group consisting of a hydrogen atom, a substituent group bonded to X via a carbon atom of said substituent group, a substituent group bonded to X via an oxygen atom of said substituent group, a substituent group bonded to X via a sulphur atom of said substituent group, and a substituent group bonded to X via a nitrogen atom of said substituent group,
y is a number from 32 to 40,
z is a number from 0 to 8,
q is a number from 0 to 16, and
m is a number representing the total positive charge m+ of n cations A and the corresponding negative charge m− of the polyanion $[M'M_{12}X_8O_yR_zH_q]$.

Embodiment 2: Polyoxometalate of embodiment 1, wherein all M are the same; preferably wherein all M are Pd or Pt, more preferably wherein all M are Pd.

Embodiment 3: Polyoxometalate of embodiment 1 or 2, wherein M' is selected from the group consisting of Ge, Sn, Pb, Sb, and Bi; more preferably wherein M' is selected from the group consisting of Ge, Sn and Pb; most preferably wherein M' is Sn.

Embodiment 4: Polyoxometalate according to any one of the preceding embodiments, wherein all M are Pd or Pt, M' is selected from the group consisting of Ge, Sn and Pb, and X is P, preferably wherein q is 0, 2, 4, 6 or 8 and z is 0, more preferably wherein q is 0 and z is 0; in particular all M are Pd, M' is Sn and X is P; more particularly wherein q is 0 and z is 0.

Embodiment 5: Polyoxometalate according to any one of the preceding embodiments, wherein
the substituent group R bonded to X via a carbon atom of said substituent group, is selected from the group consisting of
alkyl, cycloalkyl, alkenyl, cycloalkenyl, alkynyl, and aryl; wherein each of said substituent groups may be unsubstituted or substituted;
and each of said substituent groups optionally may contain one or more heteroatoms resulting in hetero-alkyl, hetero-cycloalkyl, hetero-alkenyl, hetero-cycloalkenyl, hetero-alkynyl, and hetero-aryl; and —CF$_3$, —CN, —C(O)OR$^2$, —C(O)R$^2$, and —C(O)NR$^2$R$^3$;
the substituent group R bonded to X via an oxygen atom of said substituent group, is selected from the group consisting of —OR$^2$, —O(SO$_2$)R$^2$, —O(SO)R$^2$, —O(SO$_2$)OR$^2$, —O(SO)OR$^2$, —OS(O$_2$)NR$^2$R$^3$, —OS(O)NR$^2$R$^3$, —OPO(OR$^2$)$_2$, —OPO(OR$^2$)OR$^3$, —OPO(R$^2$)OR$^3$, —OC(O)OR$^2$, —OC(O)NR$^2$R$^3$, and —OC(O)R$^2$;
the substituent group R bonded to X via a sulphur atom of said substituent group, is selected from the group consisting of —SO$_3$R$^2$, —SR$^2$, —S(O$_2$)R$^2$, —S(O)R$^2$, —S(O)OR$^2$, —S(O)NR$^2$R$^3$, and —S(O$_2$)NR$^2$R$^3$; and
the substituent group R bonded to X via a nitrogen atom of said substituent group is selected from the group consisting of —NR$^2$R$^3$, —N(R$^2$)S(O$_2$)R$^3$, —N(R$^2$)S(O$_2$)NR$^3$R$^4$, —N(R$^2$)S(O$_2$)OR$^3$, —N(R$^2$)S(O)R$^3$, —N(R$^2$)S(O)NR$^3$R$^4$, —N(R$^2$)S(O)OR$^3$, —N(R$^2$)PO(OR$^3$)$_2$, —N(R$^2$)PO(OR$^3$)OR$^4$, —N(R$^2$)PO(R$^3$)OR$^4$, —N(R$^2$)C(O)R$^3$, —N(R$^2$)C(O)OR$^3$, —N(R$^2$)C(O)NR$^3$R$^4$ and —NO$_2$;
wherein R$^2$ and R$^3$ are independently selected from the group consisting of H, alkyl, aryl, alkenyl, alkynyl, hetero-alkyl, hetero-cycloalkyl, hetero-alkenyl, hetero-cycloalkenyl, hetero-alkynyl, hetero-aryl and cycloalkyl.

Embodiment 6: Polyoxometalate according to any one of the preceding embodiments, wherein, each A is independently selected from the group consisting of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Sn, Sb, Te, phosphonium, ammonium, guanidinium, tetraalkylammonium, protonated aliphatic amines, protonated aromatic amines or combinations thereof; preferably from the group consisting of Li, K, Na and combinations thereof.

Embodiment 7: Polyoxometalate according to any one of the preceding embodiments, represented by the formula

wherein w represents the number of attracted water molecules per polyanion $[M'M_{12}X_8O_yR_zH_q]$, and ranges from 1 to 100, preferably from 10 to 60, more preferably from 20 to 50.

Embodiment 8: Polyoxometalate according to any one of the preceding embodiments, wherein the polyoxometalate is in the form of particles, preferably wherein at least 90 wt % of the polyoxometalate particles are in the form of primary particles.

Embodiment 9: Process for the preparation of the polyoxometalate according to any one of embodiments 1 to 8, said process comprising:
(a) reacting at least one source of M and at least one source of M' with at least one X-containing and optionally R-containing starting material to form a salt of the polyanion $[M'M_{12}X_8O_yR_zH_q]$ or a solvate thereof,
(b) optionally adding at least one salt of A to the reaction mixture of step (a) to form a polyoxometalate $(A_n)^{m+}[M'M_{12}X_8O_yR_zH_q]^{m-}$ or a solvate thereof, and
(c) recovering the polyoxometalate or solvate thereof.

Embodiment 10: Process according to embodiment 9, wherein in step (a) the concentration of the metal ions originating from the source of M ranges from 0.01 to 1 mole/l, the concentration of the metal ions originating from the sources of M' ranges from 0.001 to 0.1 mole/l, and the concentration of the X-containing starting material ranges from 0.001 to 1 mole/l, with the proviso that the ratio of the molar concentration of the metal ions originating from the source of M' to the molar concentration of the metal ions originating from the source of M is in the range from 1 to 20.

Embodiment 11: Process according to embodiment 9 or 10, wherein in step (a) at least one source of M is used and wherein all M are the same, preferably wherein all M are Pd.

Embodiment 12: Process according to any one of embodiments 9 to 11, wherein water is used as solvent.

Embodiment 13: Process according to embodiment 12, wherein the at least one source of M is a water-soluble salt of $Pt^{II}$ or $Pd^{II}$, preferably platinum chloride, palladium nitrate, palladium sulphate, palladium chloride or palladium acetate, in particular a water-soluble salt of $Pd^{II}$, more preferably palladium nitrate, palladium sulphate, palladium chloride or palladium acetate; the at least one source of M' is a water-soluble germanium or tin salt, preferably germanium(IV) chloride or tin(IV) chloride, in particular a water-soluble tin salt, more preferably tin(IV) chloride; and the at least one source of X is an oxide of X or a salt of $PO_4^{3-}$, preferably $As_2O_3$, $As_2O_5$, $P_2O_5$ or a salt of $PO_4^{3-}$, most preferably $NaH_2PO_4$.

Embodiment 14: Process according to any one of embodiments 9 to 13, wherein step (a) is carried out in an aqueous solution, and the pH of the aqueous solution ranges from 4 to 12, preferably from 6 to 11, and most preferred from 7 to 10.

Embodiment 15: Process according to embodiment 14, wherein in step (a) the at least one source of M, the at least one source of M', and the at least one source of X-containing and optionally R-containing starting material are dissolved in a solution of a buffer, preferably a 0.1 to 1.0 M solution of a buffer, in particular a 0.25 to 0.75 M solution of a buffer, and most preferred a 0.50 M solution of a buffer; wherein preferably the buffer is a phosphate buffer and most preferably said phosphate buffer is derived from $NaH_2PO_4$.

Embodiment 16: Process according to any one of embodiments 9 to 15, wherein in step (a) the reaction mixture is heated to a temperature of from 20° C. to 100° C., preferably from 70° C. to 90° C.

Embodiment 17: Supported polyoxometalate comprising polyoxometalate according to any one of embodiments 1 to 8 or prepared according to any one of embodiments 9 to 16, on a solid support.

Embodiment 18: Supported polyoxometalate according to embodiment 17, wherein the solid support is selected from polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous silica, zeolites, aluminophosphates (ALPOs), silicoaluminophosphates (SAPOs), metal organic frameworks (MOFs), zeolitic imidazolate frameworks (ZIFs), periodic mesoporous organosilicas (PMOs), and mixtures thereof.

Embodiment 19: Process for the preparation of supported polyoxometalate according to embodiment 17 or 18, comprising the step of contacting polyoxometalate according to any one of embodiments 1 to 8 or prepared according to any one of embodiments 9 to 16, with a solid support.

Embodiment 20: Metal cluster of the formula

[M'M°$_{12}$]

wherein
each $M^o$ is independently selected from the group consisting of $Pd^o$, $Pt^o$, $Rh^o$, $Ir^o$, $Ag^o$, and $Au^o$, preferably $Pd^o$ and $Pt^o$, most preferably $Pd^o$; in particular wherein all $M^o$ are the same, preferably wherein all $M^o$ are Pd, and
M' is selected from the group consisting of Ga, In, Tl, Ge, Sn, Pb, Sb, and Bi, and the oxidation state of M' is 0 or greater than 0, preferably M' is Sn, most preferably $Sn^o$.

Embodiment 21: Metal cluster according to embodiment 20, wherein the metal cluster is in the form of particles, preferably wherein at least 90 wt % of the metal cluster particles are in the form of primary particles.

Embodiment 22: Metal cluster according to embodiment 20 or 21, wherein the metal cluster is dispersed in a liquid carrier medium thereby forming a dispersion of metal cluster in said liquid carrier medium; and wherein preferably a dispersing agent is present to prevent agglomeration of the primary particles of metal cluster, and in particular the dispersing agent forms micelles containing one primary particle of metal cluster per micelle.

Embodiment 23: Metal cluster according to embodiment 20 or 21, wherein the metal cluster is immobilized on a solid support thereby forming supported metal cluster.

Embodiment 24: Supported metal cluster according to embodiment 23, wherein the solid support is selected from polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous silica, zeolites, aluminophosphates (ALPOs), silicoaluminophosphates (SAPOs), metal organic frameworks (MOFs), zeolitic imidazolate frameworks (ZIFs), periodic mesoporous organosilicas (PMOs), and mixtures thereof.

Embodiment 25: Process for the preparation of the dispersion of metal cluster of embodiment 22, said process comprising the steps of
(a) dissolving the polyoxometalate of any one of embodiments 1 to 8 or prepared according to any one of embodiments 9 to 16, in a liquid carrier medium,
(b) optionally providing additive means to prevent agglomeration of the metal cluster to be prepared, and
(c) subjecting the dissolved polyoxometalate to chemical or electrochemical reducing conditions sufficient to at least partially reduce said polyoxometalate into corresponding metal cluster.

Embodiment 26: Process for the preparation of the supported metal clusters of embodiment 23 or 24, comprising the steps of
(a) contacting the dispersion of metal cluster of embodiment 22 or prepared according to embodiment 25 with a solid support, thereby immobilizing at least part of the dispersed metal cluster onto the support; and
(b) optionally isolating the supported metal cluster.

Embodiment 27: Process for the preparation of the supported metal clusters of embodiment 23 or 24, comprising the steps of
(a) subjecting the supported polyoxometalate of embodiment 17 or 18 or prepared according to embodiment 19 to chemical or electrochemical reducing conditions sufficient to at least partially reduce said polyoxometalate into corresponding metal cluster; and
(b) optionally isolating the supported metal cluster.

Embodiment 28: Process according to any one of embodiments 25 or 27, wherein the chemical reducing conditions comprise the use of a reducing agent selected from organic and inorganic materials which are oxidizable by $Pd^{II}$, $Pt^{II}$, $Rh^I$, $Ir^I$, $Ag^I$ and $Ag^{III}$, and $Au^I$ and $Au^{III}$.

Embodiment 29: Process for the homogeneous or heterogeneous reductive conversion of organic substrate comprising contacting said organic substrate under addition of hydrogen with the polyoxometalate of any one of embodiments 1 to 8 or prepared according to any one of embodiments 9 to 16, and/or with the supported polyoxometalate of embodiment 17 or 18 or prepared according to embodiment 19, and/or with the metal cluster of embodiment 20 or 21, and/or with the dispersion of metal cluster of embodiment 22 or prepared according to embodiment 25 or 28, and/or with the supported metal cluster of embodiment 23 or 24 or prepared according to any one of embodiments 26 to 28.

Embodiment 30: Process according to embodiment 29, comprising:
(a) contacting a first organic substrate under addition of hydrogen with one or more optionally supported polyoxometalates and/or one or more supported metal clusters,
(b) recovering the one or more optionally supported polyoxometalates and/or the one or more supported metal clusters;
(c) contacting the one or more optionally supported polyoxometalates and/or the one or more supported metal clusters with a solvent at a temperature of 50° C. or more, and/or hydrogen stripping the one or more optionally supported polyoxometalates and/or the one or more supported metal clusters at elevated temperature, and/or calcining the one or more optionally supported polyoxometalates and/or the one or more supported metal clusters at elevated temperature under an oxygen containing gas, e.g. air, or under an inert gas, e.g. nitrogen or argon, to obtain recycled one or more optionally supported polyoxometalates and/or one or more supported metal clusters;
(d) contacting the recycled one or more optionally supported polyoxometalates and/or the one or more supported metal clusters under addition of hydrogen with a second organic substrate which may be the same as or different from the first organic substrate; and optionally repeating steps (b) to (d).

The invention claimed is:

1. A polyoxometalate represented by the formula

or solvates thereof, wherein
each A independently represents a cation and is selected from the group consisting of Li, K, Na and combinations thereof,
n is the number of cations, wherein n=8 or 12,
all M are independently selected from the group consisting of Pd and Pt, and each M has $d^8$ valence electron configuration,
M' is selected from the group consisting of Ge, Sn, and Pb,
y is a number from 32 to 40, and
m is a number representing the total positive charge m+ of n cations A and the corresponding negative charge m− of $[M'M_{12}X_8O_y]$, wherein m=8 or 12.

2. The polyoxometalate according to claim 1, represented by the formula

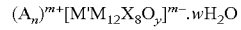

wherein w represents the number of attracted water molecules per $[M'M_{12}X_8O_y]$, and ranges from 1 to 100.

3. The polyoxometalate according to claim 1, wherein the polyoxometalate is in the form of particles.

4. A process for a preparation of the polyoxometalate according to claim 1, said process comprising:
(a) reacting at least one source of M and at least one source of M' with a X-containing starting material to form a salt of $[M'M_{12}X_8O_y]$ or solvates thereof,
(b) optionally adding at least one salt of A to the reaction mixture of step (a) to form the polyoxometalate $(A_n)^{m+}[M'M_{12}X_8O_y]^{m-}$ or solvates thereof, and
(c) recovering the polyoxometalate or solvates thereof, wherein
solvates are water is associated with the polyoxometalate,
the at least one source of M is platinum chloride, palladium nitrate, palladium sulphate, palladium chloride or palladium acetate,
the at least one source of M' is $SnCl_4$, $Sn(CH_3COO)_4$, $SnBr_4$, $Sn(NO_3)_4$, $GeCl_4$, $PbCl_4$, or $Pb(CH_3COO)_4$,
the X-containing starting material is an oxide of X or a salt of $PO_4^{3-}$,
the pH of the aqueous solution in step (a) ranges from 2 to 14, and
the reaction mixture in step (a) is heated to a temperature of from 20° C. to 100° C.

5. The process according to claim 4, wherein the at least one source of M is palladium nitrate, palladium sulphate, palladium chloride, or palladium acetate, the at least one source of M' is germanium (IV) chloride or tin(IV) chloride, and the X-containing starting material is $P_2O_5$ or a salt of $PO_4^{3-}$.

6. A supported polyoxometalate comprising the polyoxometalate according to claim 1 on a solid support.

7. A process for a preparation of a supported polyoxometalate comprising the polyoxometalate according to claim 1, said process comprising a step of contacting the polyoxometalate according to claim 1 with a solid support.

* * * * *